(12) United States Patent
Yoon et al.

(10) Patent No.: US 10,506,975 B2
(45) Date of Patent: Dec. 17, 2019

(54) BIO-SIGNAL PROCESSING APPARATUS AND BIOMETRIC INFORMATION DETECTION APPARATUS AND METHOD

(71) Applicant: SAMSUNG ELECTRONICS CO., LTD., Suwon-si (KR)

(72) Inventors: Seung Keun Yoon, Seoul (KR); Ui Kun Kwon, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 47 days.

(21) Appl. No.: 15/608,230

(22) Filed: May 30, 2017

(65) Prior Publication Data
US 2018/0146921 A1    May 31, 2018

(30) Foreign Application Priority Data
Nov. 29, 2016  (KR) .................. 10-2016-0160563

(51) Int. Cl.
*A61B 5/00* (2006.01)
*A61B 5/024* (2006.01)
*A61B 5/04* (2006.01)

(52) U.S. Cl.
CPC .......... *A61B 5/681* (2013.01); *A61B 5/02438* (2013.01); *A61B 5/02444* (2013.01);
(Continued)

(58) Field of Classification Search
CPC . A61B 5/681; A61B 5/02438; A61B 5/02444; A61B 5/04004; A61B 5/7214; A61B 5/7225; A61B 5/725; A61B 5/742
(Continued)

(56) References Cited

U.S. PATENT DOCUMENTS 5,971,930 A  10/1999 Elghazzawi
7,097,621 B2  8/2006 Narimatsu et al.
(Continued)

FOREIGN PATENT DOCUMENTS

EP   2 465 437 A2  6/2012
JP   2014-184002 A  10/2014
(Continued)

OTHER PUBLICATIONS

Communication dated Dec. 8, 2017 by the European Patent Office in counterpart European Patent Application No. 17183212.4.
(Continued)

*Primary Examiner* — Tomi Skibinski
(74) *Attorney, Agent, or Firm* — Sughrue Mion, PLLC

(57) ABSTRACT

A bio-signal processing apparatus, a biometric information detection apparatus, and a method of detecting biometric information are provided. The bio-signal processing apparatus includes a first low pass filter (LPF) configured to have a first cutoff frequency, and output a first preprocessed signal having low frequency components of an input bio-signal that are less than the first cutoff frequency, a second LPF configured to have a second cutoff frequency, and output a second preprocessed signal in which high frequency components greater than or equal to the second cutoff frequency are removed from the input bio-signal, and a processor configured to output an output bio-signal for biometric information detection, based on the output first preprocessed signal and the output second preprocessed signal.

29 Claims, 16 Drawing Sheets

(52) U.S. Cl.
CPC .......... *A61B 5/04004* (2013.01); *A61B 5/725* (2013.01); *A61B 5/7214* (2013.01); *A61B 5/7225* (2013.01); *A61B 5/742* (2013.01)

(58) Field of Classification Search
USPC ........................................................ 327/558
See application file for complete search history.

(56) References Cited

U.S. PATENT DOCUMENTS

| | | | |
|---|---|---|---|
| 7,438,688 | B2 | 10/2008 | Kobayashi et al. |
| 8,568,329 | B2 | 10/2013 | Lee et al. |
| 2003/0163287 | A1 | 8/2003 | Vock et al. |
| 2008/0027339 | A1 | 1/2008 | Nagai et al. |
| 2009/0024007 | A1 | 1/2009 | Lee et al. |
| 2012/0157857 | A1* | 6/2012 | Abe .................. A61B 7/003 600/484 |
| 2012/0330113 | A1 | 12/2012 | Kogure |
| 2015/0134080 | A1* | 5/2015 | Roh .................. B25J 9/0006 623/32 |
| 2016/0270677 | A1* | 9/2016 | Lin .................... A61B 5/02427 |

FOREIGN PATENT DOCUMENTS

| | | |
|---|---|---|
| KR | 10-0367742 B1 | 1/2003 |
| KR | 10-0866547 B1 | 11/2008 |
| WO | 2016/006468 A1 | 1/2016 |

OTHER PUBLICATIONS

L Sornmo, "Time-Varying Filtering for Removal of Baseline Wander in Exercise ECGs", Proceedings of the Computers in Cardiology Meeting, vol. Meeting 18, Sep. 23, 1991, pp. 145-148, XP010026605. (4 pages total).

* cited by examiner

BIO-SIGNAL PROCESSING APPARATUS AND BIOMETRIC INFORMATION DETECTION APPARATUS AND METHOD

CROSS-REFERENCE TO RELATED APPLICATION

This application claims priority from Korean Patent Application No. 10-2016-0160563, filed on Nov. 29, 2016 in the Korean Intellectual Property Office, the entire disclosure of which is incorporated herein by reference in its entirety.

BACKGROUND

1. Field

Apparatuses and methods consistent with exemplary embodiments relate to detecting biometric information by processing a bio-signal.

2. Description of Related Art

To measure a heart rate from a bio-signal, high frequency noise and low frequency noise may be removed from the bio-signal through low pass filtering and high pass filtering, respectively, and then a signal processing may be performed on the filtered bio-signal to measure a heart rate. In this case, a time delay may occur while the low pass filtering, the high pass filtering, and the signal processing are sequentially performed to obtain the final heart rate. Further, as a result of removing low frequency information during the filtering processes, the low frequency information cannot be used while the signal processing is performed to correct errors on the heart rate. In addition, when the low pass filtering and the high pass filtering are performed by two separate filters, a low pass filter and a high pass filter, the filters may occupy space more than is necessary because one or more identical components are contained in each of the filters.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a bio-signal processing apparatus including a first low pass filter (LPF) configured to have a first cutoff frequency, and output a first preprocessed signal having low frequency components of an input bio-signal that are less than the first cutoff frequency, a second LPF configured to have a second cutoff frequency, and output a second preprocessed signal in which high frequency components greater than or equal to the second cutoff frequency are removed from the input bio-signal, and a processor configured to output an output bio-signal for biometric information detection, based on the output first preprocessed signal and the output second preprocessed signal.

The input bio-signal may be input, in parallel, to the first LPF and the second LPF, and the first LPF and the second LPF may be further configured to filter the input bio-signal in a parallel manner.

The bio-signal processing apparatus may further include a delay buffer configured to adjust amounts of delay of the output second preprocessed signal and the output first preprocessed signal.

The delay buffer may be connected to either one or both of an input port and an output port of the second LPF.

A size of the delay buffer may be adjusted based on a difference between the first cutoff frequency and the second cutoff frequency to synchronize the output first preprocessed signal and the output second preprocessed signal.

The processor may be further configured to, in response to the first cutoff frequency and the second cutoff frequency being set to be equal, and one of the output first preprocessed signal and the output second preprocessed signal being delayed by a predetermined time relative to another one of the output first preprocessed signal and the output second preprocessed signal, through the delay buffer, compare a magnitude of the output first preprocessed signal and a magnitude of the output second preprocessed signal to generate the output bio-signal.

The processor may be further configured to determine, in the generated output bio-signal, a periodicity of a time interval in which the one of the output first preprocessed signal and the output second preprocessed signal is greater than the other of the output first processed signal and the output second preprocessed signal, and extract a cardiac contraction/relaxation cycle from the generated output bio-signal, based on the determined periodicity.

The processor may be further configured to, in response to the first cutoff frequency and the second cutoff frequency being set to be different, and the output first preprocessed signal and the output second preprocessed signal being synchronized through the delay buffer, compare a magnitude of the output first preprocessed signal and a magnitude of the output second preprocessed signal to generate the output bio-signal, and detect an error of the generated output bio-signal, based on an amount of change in time between pulse signals of the generated output bio-signal.

The processor may be further configured to, in response to the first cutoff frequency and the second cutoff frequency being set to be different, and the output first preprocessed signal and the output second preprocessed signal being synchronized through the delay buffer, generate the output bio-signal, based on a difference in magnitude between the synchronized first preprocessed signal and second preprocessed signal.

The processor may be further configured to, in response to the first cutoff frequency and the second cutoff frequency being set to be different, and one of the output first preprocessed signal and the output second preprocessed signal being delayed by a predetermined time relative to another one of the output first preprocessed signal and the output second preprocessed signal, through the delay buffer, compare a magnitude of the output first preprocessed signal and a magnitude of the output second preprocessed signal at same time points to generate the output bio-signal, determine, in the generated output bio-signal, an irregularity of a time interval in which the one of the first preprocessed signal and the second preprocessed signal is greater than the other of the first preprocessed signal and the second preprocessed signal, and extract a signal for quality assessment of the input bio-signal from the generated output bio-signal, based on the determined irregularity.

The first LPF and the second LPF may include finite impulse response (FIR) filters or infinite impulse response (IIR) filters.

The output bio-signal may include any one or any combination of a heartbeat signal, a cardiac contraction/relaxation cycle signal, a signal in which high frequency and low frequency noises are removed, the input bio-signal, and a signal for quality assessment of the input bio-signal.

The bio-signal processing apparatus further includes an integrated filter including the first LPF and the second LPF.

According to an aspect of another exemplary embodiment, there is provided a biometric information detection apparatus including a bio-signal acquirer configured to acquire a bio-signal from a subject, and a preprocessor including a first low pass filter (LPF) configured to have a first cutoff frequency, and output a first preprocessed signal having low frequency components of the acquired bio-signal that are less than the first cutoff frequency, and a second LPF configured to have a second cutoff frequency, and output a second preprocessed signal in which high frequency components greater than or equal to the second cutoff frequency are removed from the acquired bio-signal. The biometric information detection apparatus further includes a processor configured to detect biometric information, based on the output first preprocessed signal and the output second preprocessed signal.

The biometric information may include any one or any combination of a heartbeat signal, a cardiac contraction/relaxation cycle signal, a blood pressure, a degree of arterial aging, a blood sugar level, electroencephalogram (EEG), electromyography, (EMG), and electrooculogram (EOG).

The preprocessor may further include a delay buffer connected to an input port or an output port of the second LPF, and configured to adjust amounts of delay of the output first preprocessed signal and the output second preprocessed signal.

The first LPF and the second LPF may be implemented independently, and further configured to filter the acquired bio-signal in a parallel manner.

The first LPF and the second LPF may be implemented as an integrated filter into which the first and second LPFs are combined, and further configured to integrally filter the acquired bio-signal.

The bio-signal acquirer may be further configured to acquire the bio-signal by emitting light to the subject and detecting light scattered or reflected from the subject.

The biometric information detection apparatus may further include a communication interface configured to receive bio-signal data that is stored in an external storage device, and a display configured to display the acquired bio-signal, the output first preprocessed signal, the output second preprocessed signal, and the detected biometric information.

According to an aspect of another exemplary embodiment, there is provided a method of detecting biometric information including acquiring a bio-signal from a subject, outputting, by a first low pass filter (LPF), a first preprocessed signal having low frequency components of the acquired bio-signal that are less than a first cutoff frequency, outputting, by a second LPF, a second preprocessed signal in which high frequency components greater than or equal to a second cutoff frequency are removed from the acquired bio-signal, and detecting biometric information, based on the output first preprocessed signal and the output second preprocessed signal.

The method may further include displaying the acquired bio-signal, the output first preprocessed signal, the output second preprocessed signal, and the detected biometric information.

The method may further include adjusting, by a delay buffer, amounts of delay of the output second preprocessed signal and the output first preprocessed signal.

According to an aspect of another exemplary embodiment, there is provided a wearable device including a sensor configured to detect a bio-signal of a user, a processor configured to control the sensor to detect the bio-signal, filter the detected bio-signal through an LPF, adjust an amount of delay of the filtered bio-signal, and detect biometric information, based on the filtered bio-signal of which the amount of delay is adjusted, and a main body in which the sensor and the processor are disposed.

The wearable device may further include a communication interface disposed in the main body, and configured to receive biometric information from a biometric information database (DB). The processor may be further configured to control the communication interface to transmit the detected biometric information to the biometric information DB.

The wearable device may further include a display disposed in the main body, and configured to display the detected biometric information.

The processor may include the LPF and another LPF that include finite impulse response (FIR) filters or infinite impulse response (IIR) filters, and a delay buffer configured to adjust amounts of delay of outputs of the LPF and the other LPF, and the processor may be further configured to filter the detected bio-signal through the other LPF.

The processor may be further configured to control the sensor to, based on a result of assessing a quality of the detected bio-signal, re-detect a bio-signal of the user.

According to an aspect of another exemplary embodiment, there is provided a bio-signal processing apparatus including a first low pass filter (LPF) configured to filter an input bio-signal to generate a first preprocessed signal having low frequency components of the input bio-signal that are less than a first cutoff frequency, a second LPF configured to filter the input bio-signal to generate a second preprocessed signal in which high frequency components greater than or equal to a second cutoff frequency are removed from the input bio-signal, a delay buffer configured to delay one of the generated first preprocessed signal and the generated second preprocessed signal, and a processor configured to generate an output bio-signal for biometric information detection, based on the delayed one of the output first preprocessed signal and the output second preprocessed signal and another one of the output first preprocessed signal and the output second preprocessed signal.

The first cutoff frequency may be different than the second cutoff frequency, the delay buffer may be further configured to delay the generated second preprocessed signal to synchronize the generated second preprocessed signal with the generated first preprocessed signal, and the processor may be further configured to invert the generated first preprocessed signal, and add the inverted first preprocessed signal to the synchronized second preprocessed signal to generate a band pass filtered signal as the output bio-signal.

The first cutoff frequency may be different than the second cutoff frequency, the delay buffer may be further configured to delay the generated second preprocessed signal to synchronize the generated second preprocessed signal with the generated first preprocessed signal, and the processor may be further configured to compare the generated first preprocessed signal to the synchronized second preprocessed signal to generate a pulse signal as the output bio-signal.

The first cutoff frequency may be equal to the second cutoff frequency, the delay buffer may be further configured to delay the generated second preprocessed signal by a predetermined amount of time, and the processor may be further configured to compare the generated first preprocessed signal to the delayed second preprocessed signal to generate a pulse signal as the output bio-signal.

The first cutoff frequency may be different than the second cutoff frequency, the delay buffer may be further configured to delay the generated second preprocessed signal by a predetermined amount of time, and the processor may be further configured to compare the generated first preprocessed signal to the delayed second preprocessed signal to generate a pulse signal as the output bio-signal.

BRIEF DESCRIPTION OF THE DRAWINGS

The above and/or other aspects will be more apparent by describing exemplary embodiments with reference to the accompanying drawings, in which.

DETAILED DESCRIPTION

Figure 1:
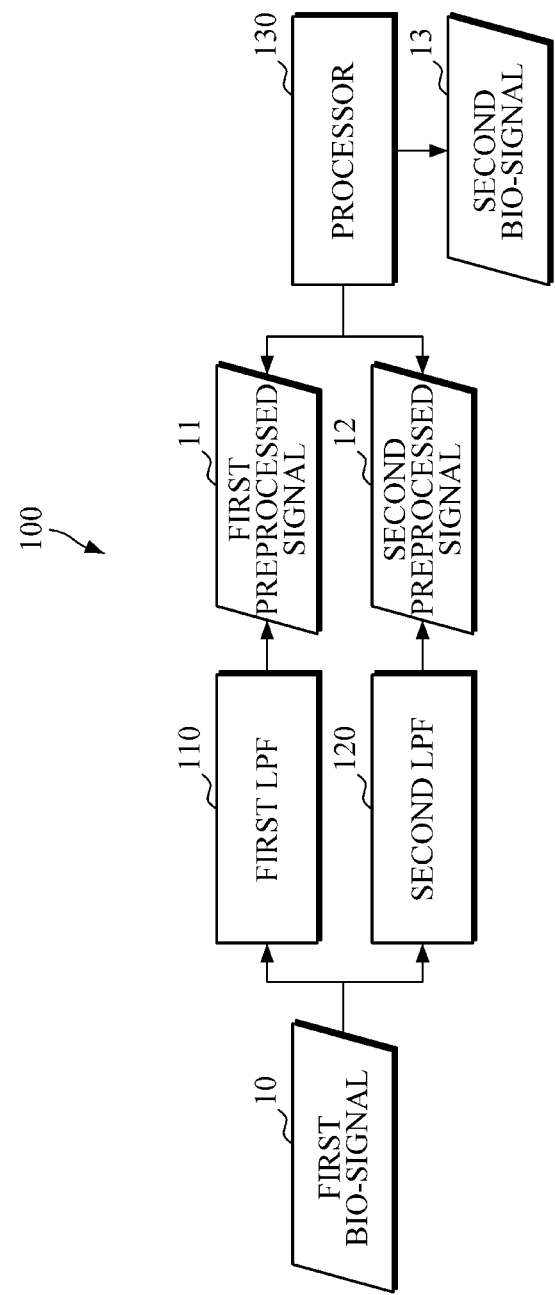
FIG. 1 is a block diagram illustrating a bio-signal processing apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

The use of the terms "first," "second," and the like does not imply any particular order, but they are included to identify individual elements. Moreover, the use of the terms first, second, etc. does not denote any order or importance, but rather the terms first, second, etc. are used to distinguish one element from another. It will be understood that the terms "comprises," "comprising," "includes" and/or "including" when used in this specification, specify the presence of stated elements, but do not preclude the presence or addition of one or more other elements. Terms such as "unit" and "module" denote units that process at least one function or operation, and they may be implemented by using hardware, software, or a combination of hardware and software.

Figure 2:
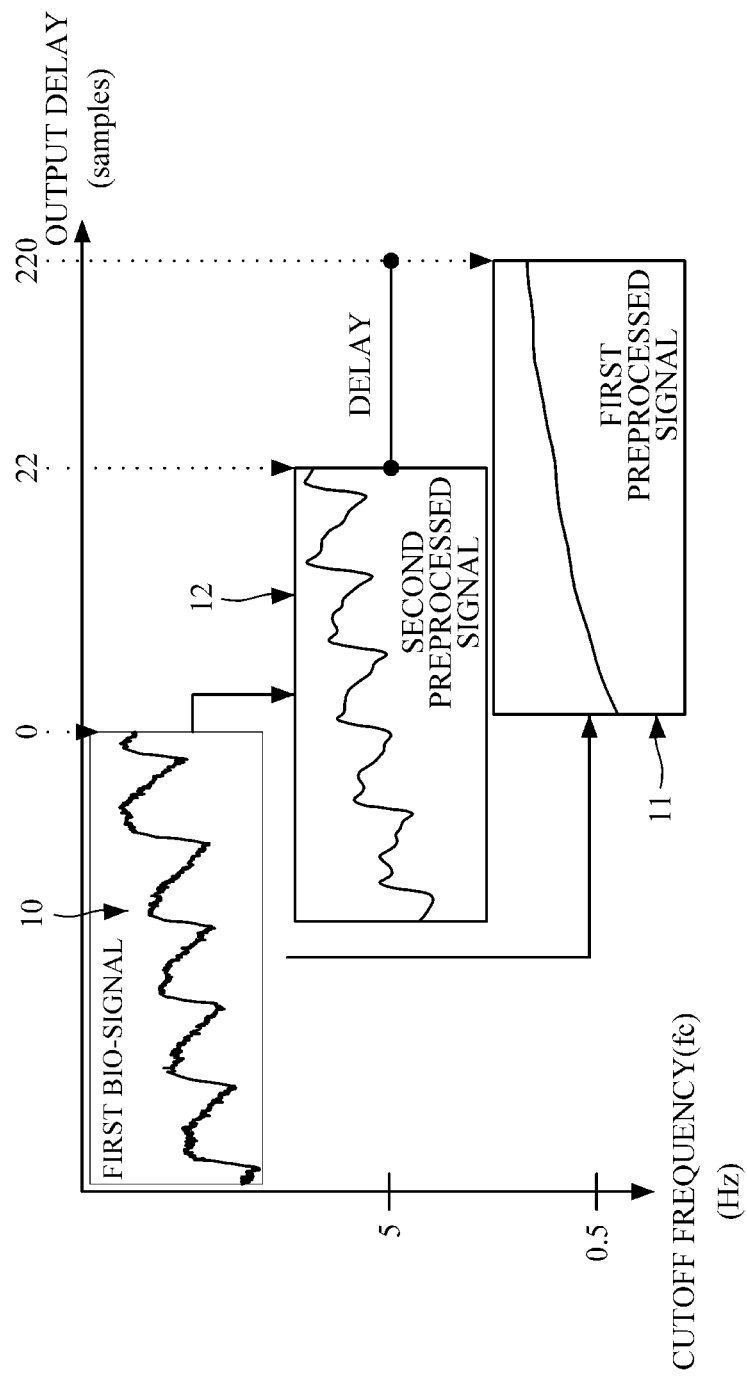
FIG. 2 is a graph illustrating outputs of low pass filters (LPFs) that have different cutoff frequencies.

FIG. 1 is a block diagram illustrating a bio-signal processing apparatus according to an exemplary embodiment. FIG. 2 is a graph illustrating outputs of low pass filters (LPFs) that have different cutoff frequencies. Referring to FIG. 1, a bio-signal processing apparatus 100 includes a first LPF 110, a second LPF 120, and a processor 130. In this case, the processor 130 may be implemented with one or more processors, memories, and one or more modules including them. The bio-signal may include a bioelectrical signal, a biomechanical signal, a bio-acoustic signal, and a bio-optical signal.

The first LPF 110 may be set to have a first cutoff frequency and output a first preprocessed signal 11 with low frequency components from an input first bio-signal 10. For example, the first LPF 110 may be set to have a cutoff frequency $f_{c1}$ of 0.5 Hz, and output the first preprocessed signal 11 by blocking a frequency band of 0.5 Hz or greater and passing only low frequency components less than 0.5 Hz.

The second LPF 120 may be set to have a second cutoff frequency and output a second preprocessed signal 12 by removing high frequency components from the first bio-signal 10. For example, the second LPF 120 may be set to have a cutoff frequency $f_{c2}$ of 5 Hz, and output the second preprocessed signal 12 in which high frequency components of 5 Hz or greater are filtered out.

When the processor 130 is designed to use a frequency band (e.g., frequency band from 0.7 Hz to 4.8 Hz) of the first bio-signal 10, the first cutoff frequency $f_{c1}$ (e.g., 0.5 Hz) may be set to be less than or equal to a lower limit of the frequency band (e.g., 0.7 Hz), and the second cutoff frequency $f_{c2}$ (e.g., 5 Hz) may be set to greater than or equal to an upper limit of the frequency band (e.g., 4.8 Hz).

The first LPF 110 and the second LPF 120 may be connected in parallel with each other, and the first bio-signal 10 may be simultaneously input to both the first LPF 110 and the second LPF 120. The first LPF 110 and the second LPF 120 may filter the input first bio-signal in a parallel manner and output the first preprocessed signal 11 and the second preprocessed signal 12, respectively. As such, the preprocessed signals output through parallel processing may be input to the processor 130 so that the delay between the input signals and the output signals of the filters may be effectively managed.

The processor 130 may output a second bio-signal 13 for biometric information detection on the basis of the first preprocessed signal 11 and the second preprocessed signal 12. For example, the processor 130 may use the first preprocessed signal 11 and the second preprocessed signal 12 that are filtered, respectively, by the first LPF 110 and the second LPF 120 that has the same or different cutoff frequency from the first LPF 110, and output a band pass filtered signal for bio-signal detection, a pulse signal, a low pass filtered signal, and a signal for quality assessment.

For example, the lower the cutoff frequency of the LPF is set, the more delayed the output of the filter may be. In one example, in the case in which the first cutoff frequency of the first LPF 110 is set to 0.5 Hz and the second cutoff frequency of the second LPF 120 is set to 5 Hz, the first preprocessed signal 11 of the first LPF 110, which has a lower cutoff frequency, may be delayed relative to the second preprocessed signal 12 of the second LPF 120, and then output.

Referring to FIGS. 1 and 2, it is assumed that the first cutoff frequency of the first LPF 110 is set to 0.5 Hz and the second cutoff frequency of the second LPF 120 is set to 5 Hz. In this case, when the first bio-signal 10 is input to the bio-signal processing apparatus 100, the first preprocessed signal 11 and the second preprocessed signal 12, each passing through the filter with the passband of the set cutoff frequency, may have a delay due to the difference between the cutoff frequencies. For example, as shown in FIG. 2, when the first preprocessed signal 11 and the second preprocessed signal 12 may be delayed by 220 samples and 22 samples, respectively, relative to the first bio-signal 10, and output, the first preprocessed signal 11 is delayed by 198 samples relative to the second preprocessed signal 12 and output so that the two output signals may be output in a non-synchronized state.

In this case, the bio-signal processing apparatus 100 may output a second bio-signal 13 for bio-signal detection by adjusting the delay of preprocessed signals. Here, the second bio-signal may include various preprocessed signals including a heartbeat signal, a signal in which high frequency and low frequency noises are removed, the input first bio-signal, and a signal for quality assessment of the input first bio-signal.

For example, the bio-signal processing apparatus 100 may adjust the amount of delay of the preprocessed signals by connecting a delay buffer to input ports and/or output ports of the first LPF and the second LPF. In this case, the LPF connected with the delay buffer to delay an output may be a delay LPF (DLPF). The DLPF and the LPF may be designed to share a buffer with each other, and the configuration for adjusting the amount of delay of output by sharing the buffer will be described below.

Figure 3:
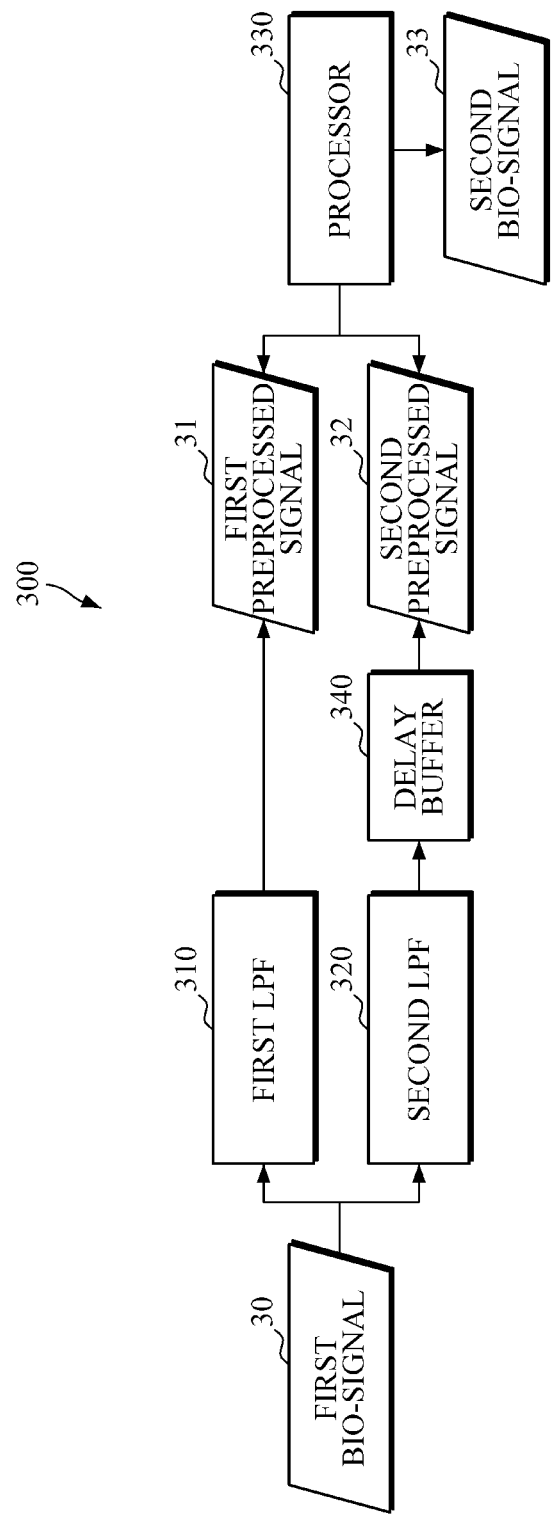
FIG. 3 is a block diagram illustrating a bio-signal processing apparatus according to another exemplary embodiment.

FIG. 3 is a block diagram illustrating a bio-signal processing apparatus according to another exemplary embodiment. FIGS. 4A, 4B, 4C, and 4D are graphs for describing processing of a bio-signal, according to exemplary embodiments of FIG. 3. FIGS. 4A to 4D illustrate preprocessed signals according to a cutoff frequency $f_c$ and an amount of delay d when a first bio-signal 30 is input at a sampling frequency $f_s$ of 250 Hz.

Referring to FIG. 3, a bio-signal processing apparatus 300 includes a first LPF 310, a second LPF 320, a processor 330, and a delay buffer 340. Here, the first LPF 310, the second LPF 320, and the processor 330 perform substantially the same functions as the first LPF 110, the second LPF 120, and the processor 130 of FIG. 1, and thus the following description will focus on configurations that are not duplicated.

Although FIG. 3 illustrates, as an example, the delay buffer 340 connected to an output end of the second LPF 320, the delay buffer 340 may be connected to either one or both of an input port and an output port of the first LPF and/or the second LPF, and the amount of delay of an output signal may be adjusted according to the purpose of use of the output signal, such as detection of a pulse wave signal, implementation of a band pass filter, and quality assessment of the output signal.

For example, referring to FIGS. 2 and 3, when it is assumed that a cutoff frequency of the first LPF 310 is set to 0.5 Hz, a cutoff frequency of the second LPF 320 is set to 5 Hz, and a first preprocessed signal 31 and a second preprocessed signal 32 are output, the first preprocessed signal 31 and the second preprocessed signal 32 are delayed by 220 samples and 22 samples, respectively, relative to the first bio-signal 30, and then are output, so that the first preprocessed signal 31 is delayed by 198 samples relative to the second preprocessed signal 32, and then is output.

In this case, the delay buffer 340 may delay the preprocessed signals by a predetermined sampling period, based on the amount of delay of each preprocessed signal, and may control a degree of delay between the output signals. The size of the delay buffer 340 may be determined based on a difference between cutoff frequencies set for the filters (e.g., the first LPF 310 and the second LPF 320). In addition, the size of the delay buffer 340 may be automatically determined on the basis of the difference between the cutoff frequencies or may be determined by a user or an operator. For example, when the first preprocessed signal 31 is delayed by 220 samples and then is output, the delay buffer 340 may be connected to the input port and/or the output port of the second LPF 320 and adjust a delay between the first preprocessed signal 31 and the second preprocessed signal 32 to synchronize the two output signals with each other. In this case, the size of the delay buffer for synchronization may be automatically determined based on the cutoff frequency difference.

The processor 330 may output a second bio-signal 33 for biometric information detection using the delay-adjusted signal.

Figure 4A:
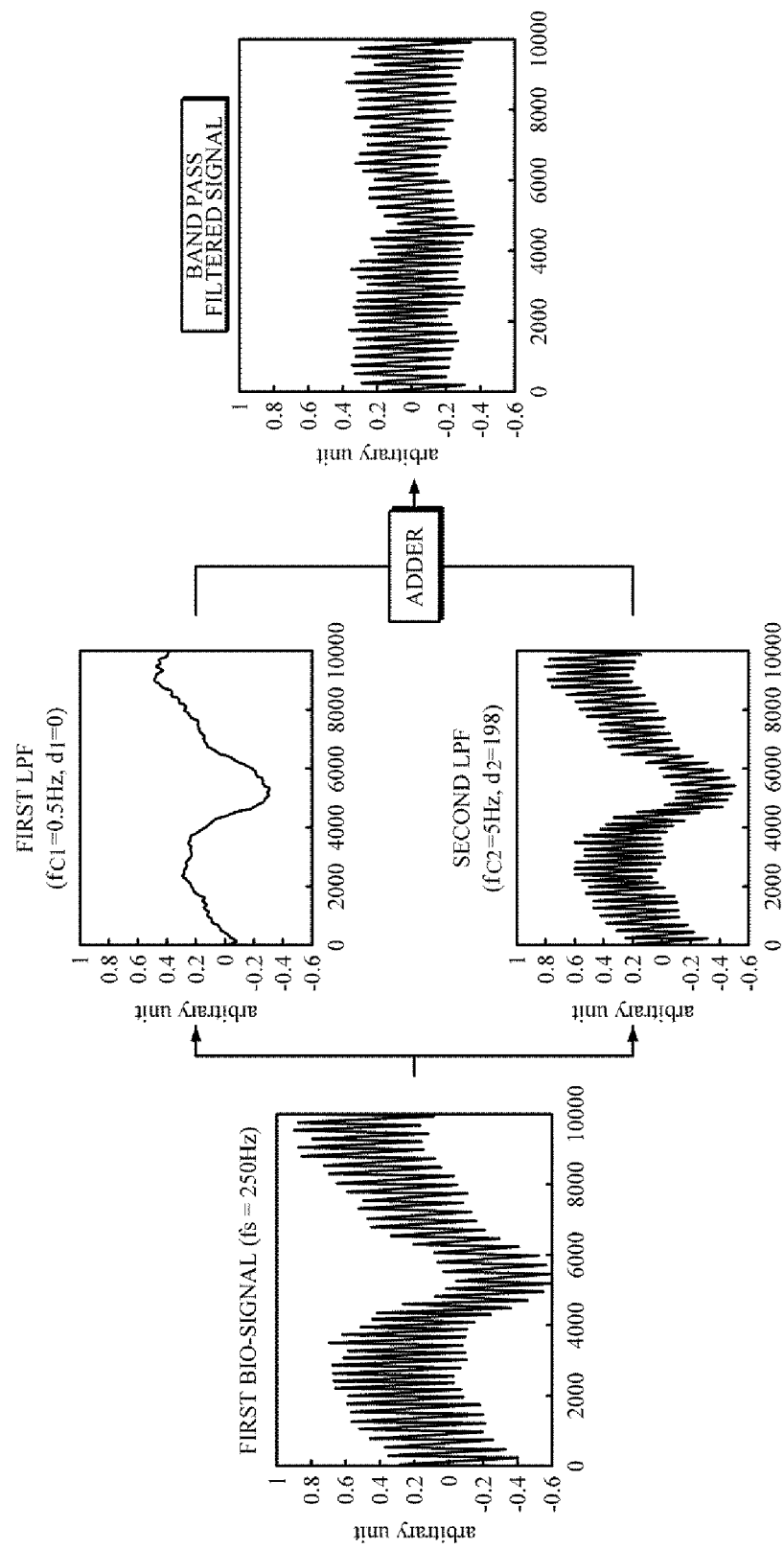
FIG. 4A is a graph for describing processing of a bio-signal, according to the exemplary embodiment of FIG. 3.

For example, referring to FIGS. 3 and 4A, the bio-signal processing apparatus 300 may output the band pass filtered signal in which low frequency and high frequency noises are removed by synchronizing the first preprocessed signal and the second preprocessed signal as the second bio-signal 33. In one example, when the first cutoff frequency and the second cutoff frequency are set differently and the first preprocessed signal and the second preprocessed signals are synchronized with each other and output through the delay buffer, the processor 330 may extract the band pass filtered signal in which low frequency and high frequency noises are removed on the basis of a difference in magnitude between the first preprocessed signal and the second preprocessed signal. For example, in the case in which the cutoff frequency of the first LPF 310 is 0.5 Hz and the cutoff frequency of the second LPF 320 is 5 Hz, the delay buffer 340 may be connected to the input port and/or the output port of the second LPF 320 such that a signal is delayed by 198 samples with respect to the delay of the first preprocessed signal and then is output.

Figure 4B:
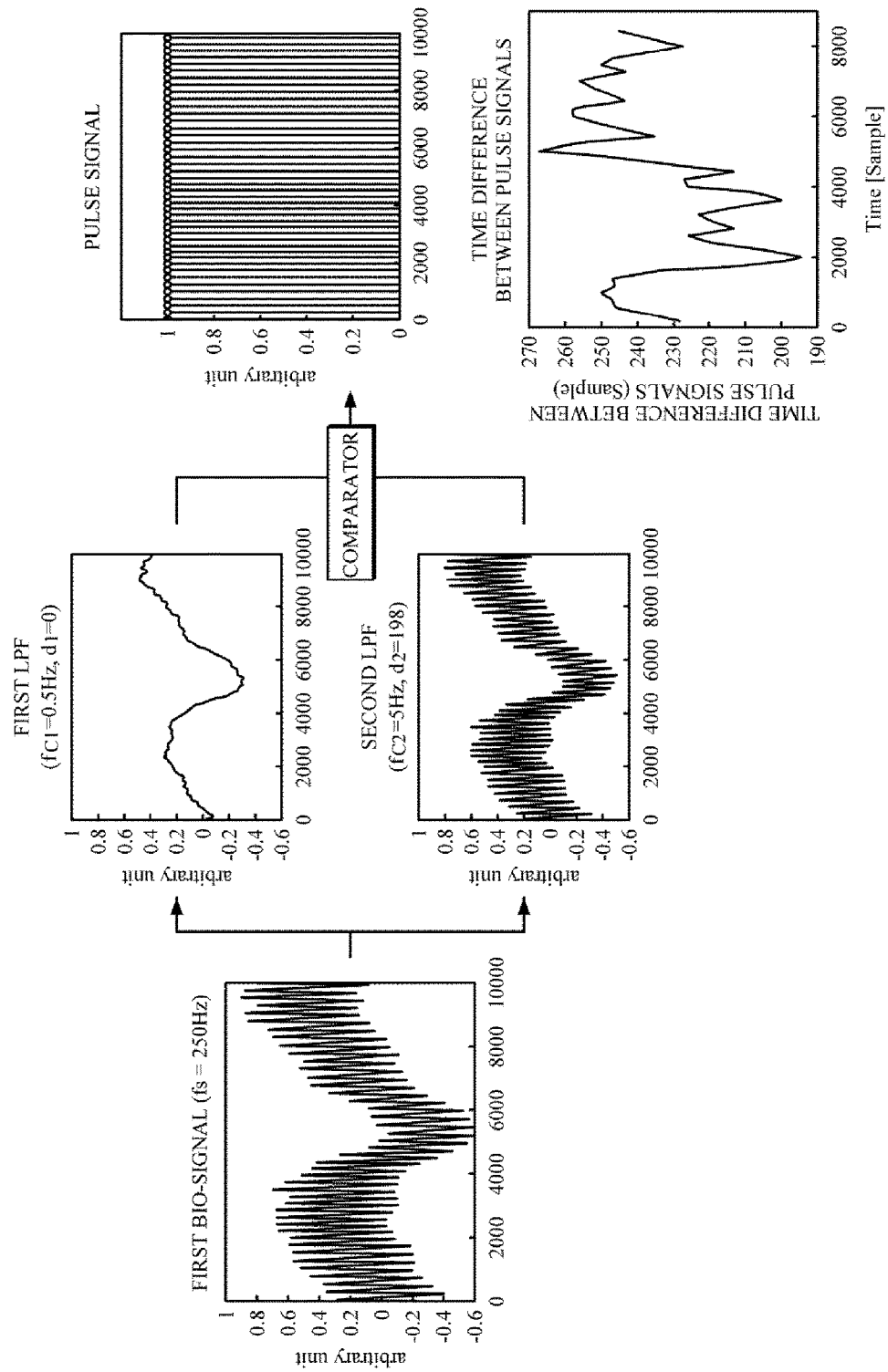
FIG. 4B is a graph for describing processing of a bio-signal, according to another exemplary embodiment of FIG. 3.

In this case, the processor 330 may output the second bio-signal 33 having a pass band of 0.5 Hz to 5 Hz by removing the first preprocessed signal 31 from the second preprocessed signal 32. Once the second preprocessed signal 32 that is output from the second LPF 320 is delayed through the delay buffer 340, the second preprocessed signal 32 may become synchronized with the first preprocessed signal 31. Upon receiving the synchronized first and second preprocessed signals 31 and 32, the processor 330 may invert the first preprocessed signal 31 with respect to a time axis (e.g., x-axis) and may add the inverted first preprocessed signal 31 and the second preprocessed signal 32 to obtain a band pass signal from which high frequency and low frequency noises are removed. The band pass signal may correspond to the second bio-signal 33. In this case, the processor 330 may include one or more adders to carry out summation. For example, because a pulse signal has a frequency of about 0.83 Hz to 3.33 Hz, 50 to 200 cycles per minute, an output of the processor 330 having a corresponding frequency may be used to detect the pulse signal. FIG. 4B is a graph for describing bio-signal processing of a bio-signal processing apparatus 300 according to another exemplary embodiment.

In another example, referring to FIGS. 3 and 4B, the bio-signal processing apparatus 300 may synchronize the first preprocessed signal 31 and the second preprocessed signal 32 with each other, and detect an error of the second bio-signal that is extracted using the first preprocessed signal 31 and a pulse signal obtained by comparing the magnitudes of the first preprocessed signal 31 and the second preprocessed signal 32.

For example, the processor 330 may calculate a time interval between the pulse signals, and detect an error of the detected heartbeat signal on the basis of a change in the time interval of the pulse signal. In one example, referring to FIG. 4B that illustrates a graph showing a time difference between the pulse signals, a time difference between the pulse signals rapidly changes in the interval of about 4500 to 5000 samples. In this case, the processor 330 may classify a signal in the interval in which the time interval between the pulse signals abruptly changes as a noise component, such as motion noise, and detect the signal as an error.

Figure 4C:
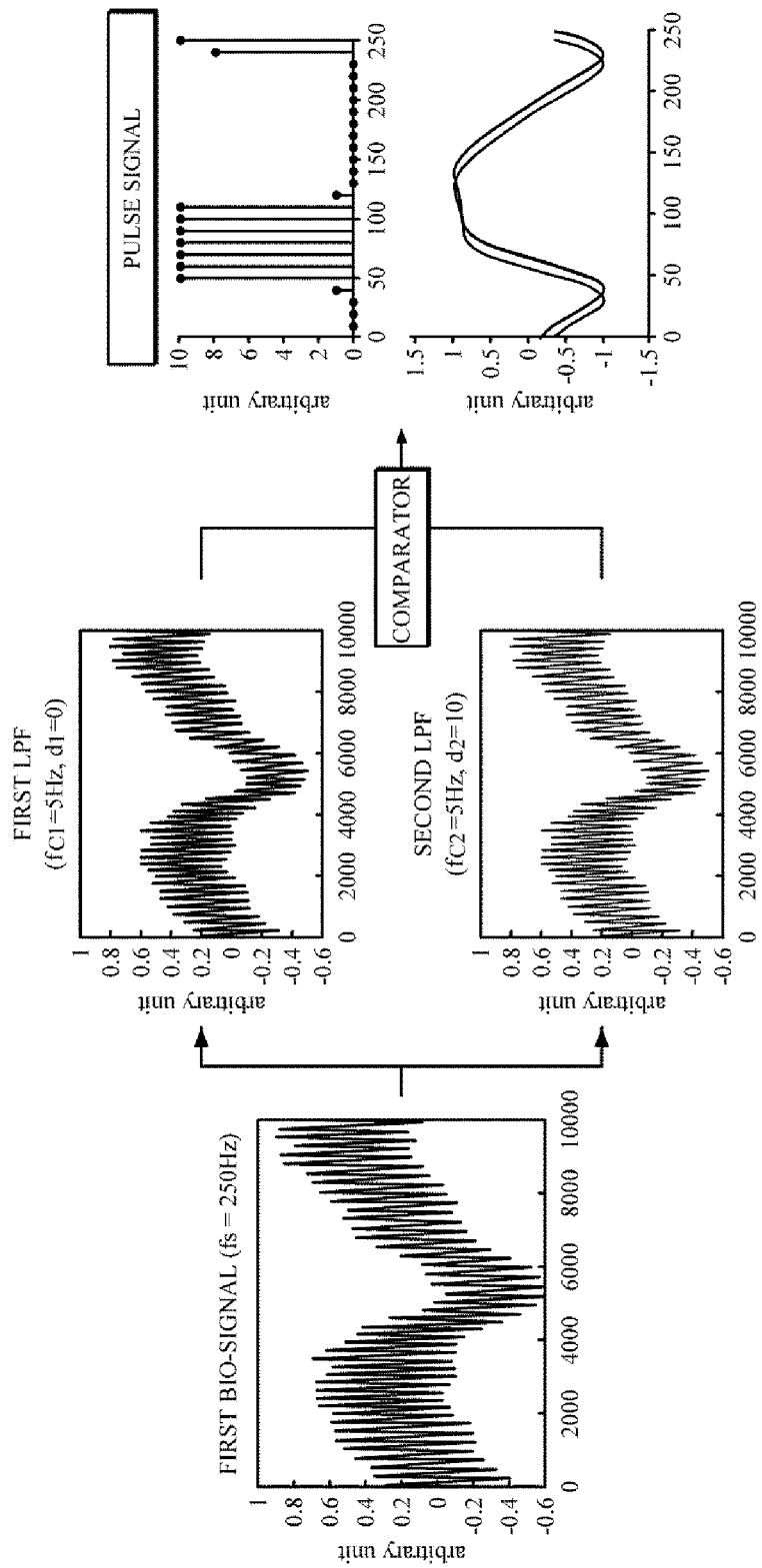
FIG. 4C is a graph for describing processing of a bio-signal, according to another exemplary embodiment of FIG. 3.

In another example, referring to FIGS. 3 and 4C, the bio-signal processing apparatus 300 may output the second bio-signal 33 for extracting a heartbeat signal by adjusting the amounts of delay of the first preprocessed signal and the second preprocessed signal and comparing the magnitudes of the first preprocessed signal 31 and the second preprocessed signal 32. For example, when the first cutoff frequency and the second cutoff frequency are set to the same frequency, and one of the first preprocessed signal 31 and the second preprocessed signal 32 is delayed by a predetermined time relative to the other signal and is output, the processor 330 may extract the second bio-signal 33 on the basis of a comparison of magnitudes between the first preprocessed signal 31 and the second preprocessed signal 32 at the same time point with respect to the time axis.

In one example, when the first LPF 310 and the second LPF 320 have the same cutoff frequency of 5 Hz, the delay buffer 340 may be connected to the second LPF 320 such that an output of the second LPF 320 is delayed by 10 samples relative to the first preprocessed signal.

In this case, the processor 330 may determine a period of the interval in which one of the first preprocessed signal 31 and the second preprocessed signal 32 is greater than the other processed signal at the same time point with respect to the time axis, and may extract a cardiac contraction/relaxation cycle from the second bio-signal 33 on the basis of the determined periodicity.

In one example, when the first preprocessed signal 31 and the second preprocessed signal 32, which are generated by removing high frequency noise from the first bio-signal 30, are set to have a predetermined difference (e.g., 10 samples) therebetween and the processor 330 may extract only a region in which the first preprocessed signal 31 is greater than the second preprocessed signal 31 using a comparator, in the case of a heartbeat signal having a regular period, a pulse signal having a periodicity may be extracted. In this case, the processor 330 may output the extracted pulse signal as the second bio-signal 33 for extracting heartbeats of the user or a cardiac contraction/relaxation cycle signal.

Although for convenience of description, it is described that the region in which the first preprocessed signal 31 is greater than the second preprocessed signal 32 is extracted, the region in which the second preprocessed signal 32 is greater than the first preprocessed signal 31 may be extracted, and the extraction of the pulse signal through the comparison of the magnitudes of the preprocessed signals may be set differently depending on a bio-signal to be detected or the purpose of operation of the bio-signal processing apparatus 300.

Figure 4D:
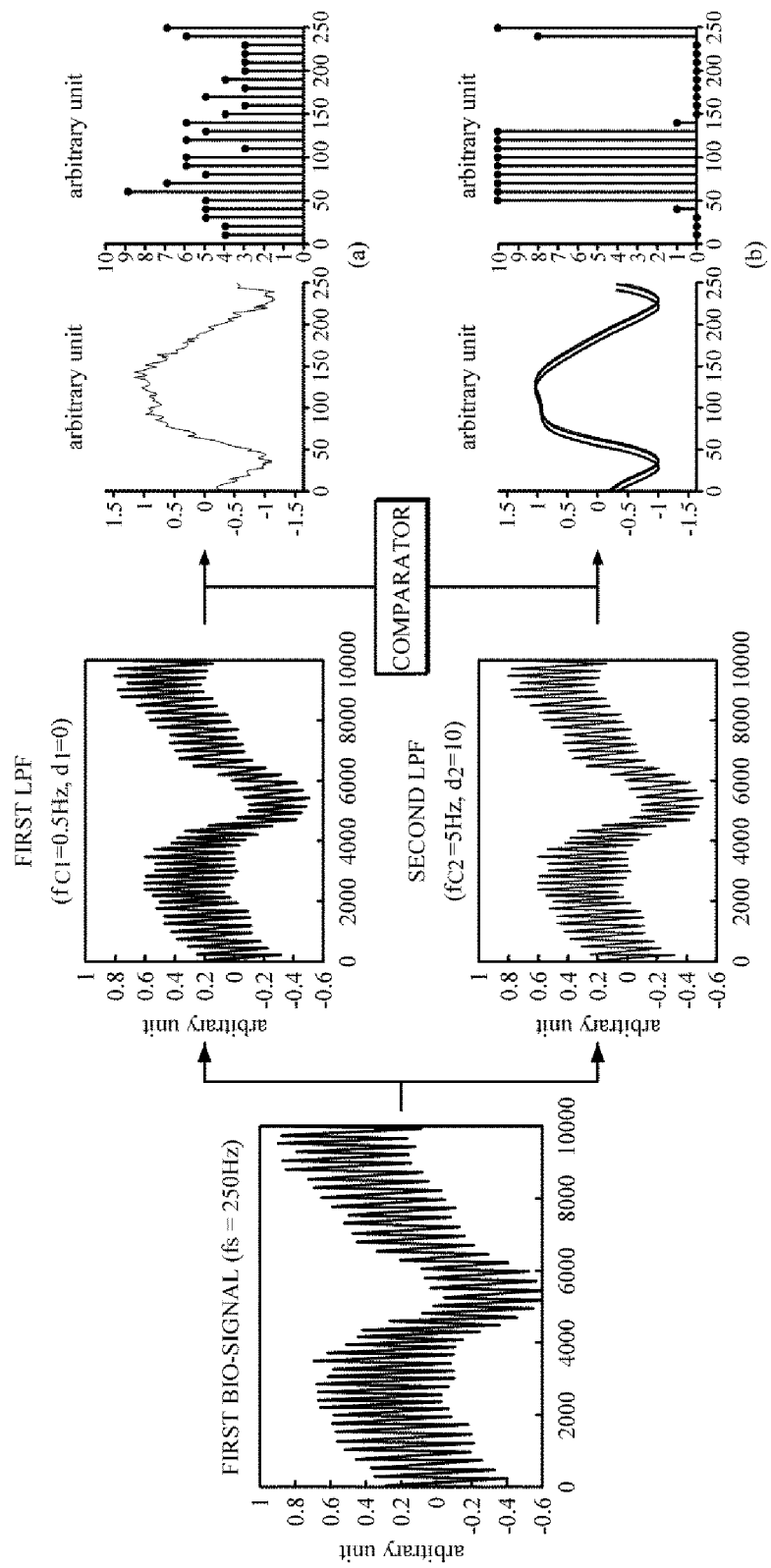
FIG. 4D is a graph for describing processing of a bio-signal, according to another exemplary embodiment of FIG. 3.

In another example, referring to FIGS. 3 and 4D, the bio-signal processing apparatus 300 may output the second bio-signal 33 for assessing a quality of the first bio-signal by adjusting the amounts of delay of the first preprocessed signal 31 and the second preprocessed signal 32 and comparing the magnitudes of the first preprocessed signal 31 and the second preprocessed signal 32. For example, when the first cutoff frequency and the second cutoff frequency are set differently and one of the first preprocessed signal 31 and the second preprocessed signal 32 is delayed by a predetermined time relative to the other processed signal and output through the delay buffer, the processor 330 may determine irregularity of the interval in which one of the first preprocessed signal 31 and the second preprocessed signal 32 is greater than the other by comparing the magnitudes of the first preprocessed signal 31 and the second preprocessed signal 32, and may extract a signal for assessing a quality of the first bio-signal from the second bio-signal 33 on the basis of the determined irregularity.

In one example, the first LPF 310 may act as an all pass filter or output the entire first bio-signal. When the cutoff frequency of the second LPF 320 is set to 5 Hz, the delay buffer 340 may be connected to the input port and/or the output port of the second LPF 320 so that the output from the second LPF 320 is synchronized with the first preprocessed signal 31.

In this case, the processor 330 may compare the magnitude of the second preprocessed signal 32, which has been synchronized with the first preprocessed signal 31 by adjusting the amount of delay thereof, with the magnitude of the first preprocessed signal 31 to calculate the region in which the first preprocessed signal 31 is greater than the second preprocessed signal 32, and may extract a signal for assessing a quality of the first bio-signal 30 on the basis on the irregularity of the calculated area.

In one example, when the first bio-signal 30 contains high frequency noise, such as motion noise, and the signal quality of the first bio-signal 30 is hence poor, the comparison result of the first preprocessed signal 31 and the second preprocessed signal 32 may be extracted with an irregular pattern as shown in diagram (a) of FIG. 4D. When the first bio-signal 30 does not contain any noise and the signal quality of the first bio-signal 30 is hence good, the comparison result of the first preprocessed signal 31 and the second preprocessed signal 32 may appear in the form of a pulse similar to a periodic heartbeat signal as shown in diagram (b) of FIG. 4D. As such, the processor 330 may output the second bio-signal 33 for determining the signal quality of the first bio-signal obtained by comparing the magnitudes of the first preprocessed signal 31 and the second preprocessed signal 32 that are synchronized with each other.

Figure 5:
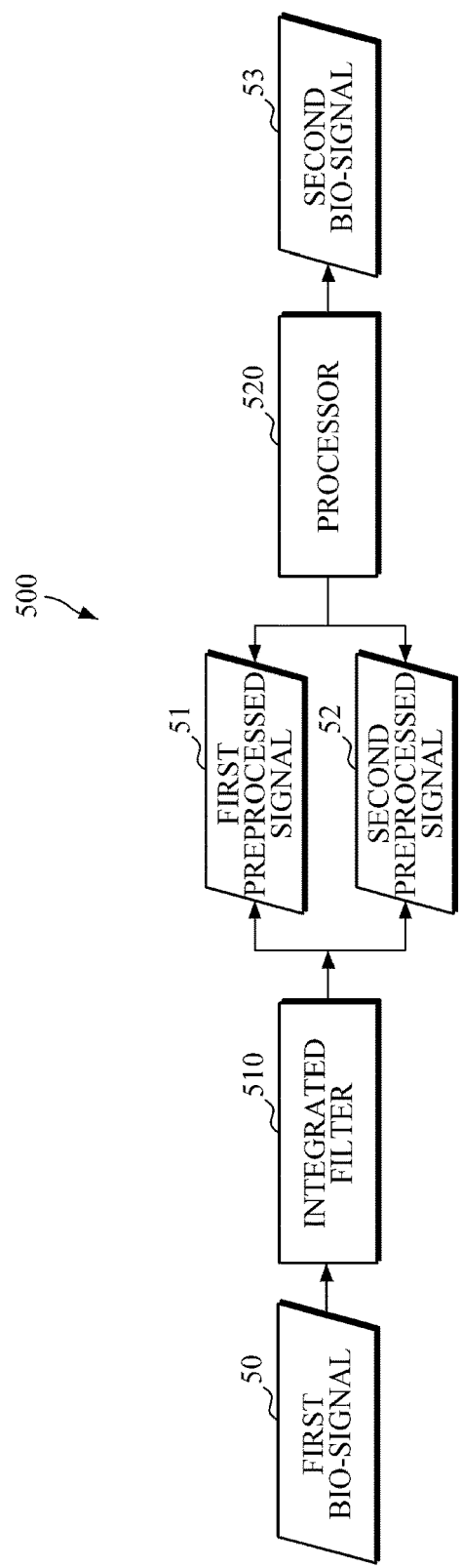
FIG. 5 is a block diagram illustrating a bio-signal processing apparatus according to another exemplary embodiment.

FIG. 5 is a block diagram illustrating a bio-signal processing apparatus according to another exemplary embodiment. Referring to FIG. 5, a bio-signal processing apparatus 500 includes an integrated filter 510 and a processor 520.

The integrated filter 510 may be configured by connecting a delay buffer to two or more LPFs to adjust delays of signals output from the respective two or more LPFs, and may output a first preprocessed signal 51 that includes low frequency components of an input first bio-signal 50 and a second preprocessed signal 52 in which high frequency components of the first bio-signal 50 are filtered out.

For example, the integrated filter 510 may include two or more LPFs that are set to have different cutoff frequencies. Due to LPF characteristics, output signals of LPFs are delayed longer as the lower cutoff frequency of the LPFs becomes lower. Thus, the outputs of the two or more LPFs set to have different cutoff frequencies may be output by varying the amounts of delay thereof according to a difference between the set cutoff frequencies.

The integrated filter 510 may include delay buffers for adjusting the amounts of delay of signals to be output from the respective two or more LPFs. Here, the delay buffer may be connected to an input port and/or an output port of the LPF and may adjust the amount of delay of the output. In this case, the amount of delay may be adjusted in units of samples by adjusting the size N of the delay buffer, and the LPF to which the delay buffer is connected may be referred to as a DLPF.

For example, the integrated filter 510 may synchronize the first preprocessed signal 51 and the second preprocessed signal 52 with each other by adjusting the size of the delay buffer on the basis of a difference between the cutoff frequencies. In one example, when it is assumed that the integrated filter 510 includes the first LPF set to have a cutoff frequency of 0.5 Hz and the second LPF set to have a cutoff frequency of 5 Hz and the output of the first LPF is delayed by 220 samples relative to the first bio-signal and the output of the second LPF is delayed by 22 samples, the output of the second LPF is further delayed by 198 samples (220 samples–22 samples) in order that the output of the first LPF is synchronized with the output of the second LPF. In this case, the delay buffer is connected to the input port and/or the output port of the second LPF such that the output of the second LPF is further delayed by 198 samples (220 samples–22 samples). Accordingly, the output (e.g., the first preprocessed signal) of the first LPF and the output (e.g., the second preprocessed signal) of the second LPF can be synchronized with each other.

The integrated filter 510 may include two or more LPFs. For example, under the assumption that the integrated filter 510 includes a first LPF having a cutoff frequency of 0.5 Hz, a second LPF having a cutoff frequency of 5 Hz, and a third LPF having a cutoff frequency of 50 Hz, the output of the first LPF may be delayed by 220 samples, the output of the second LPF may be delayed by 22 samples, and the output of the third LPF may be delayed by 2 samples relative to the first bio-signal input.

In this case, in order for the outputs of the second LPF and the third LPF to be synchronized with each other with reference to the output of the first LPF, the output of the second LPF is further delayed by 198 samples (220 samples–22 samples), and the output of the third LPF is further delayed by 218 samples (220 samples–2 samples).

In the integrated filter 510, the delay buffer may be connected to the input port and/or the output port of the second LPF to delay the output of the second LPF by 198 samples (220 samples–22 samples), and the delay buffer may be connected to the input port and/or the output port of the third LPF to delay the output of the third LPF by 218 samples (220 samples–2 samples), so that the output (e.g., a first preprocessed signal) of the first LPF, the output (e.g., a second preprocessed signal) of the second LPF, and the output (e.g., a third preprocessed signal) of the third LPF may be synchronized with one another.

In another example, in the case in which the integrated filter 510 includes a first LPF having a cutoff frequency of 0.5 Hz and a second LPF having a cutoff frequency of 5 Hz, an output of the first LPF may be delayed by 220 samples, and an output of the second LPF may be delayed by 22 samples relative to a first bio-signal input. In this case, the integrated filter 510 may adjust the amount of delay of the output of the second LPF so that the output of the first LPF and the output of the second LPF differ by 10 samples. That is, the integrated filter 510 may adjust the amount of delay of the output of the second LPF to allow the output of the second LPF to differ by 10 samples from the output of the first LPF by connecting the delay buffer to the input port and/or the output port of the second LPF so that the output of the second LPF is delayed by 188 samples or 208 samples.

The filters included in the integrated filter 510 may be connected with delay buffers according to the purpose of signal processing so that the amounts of delay of the filters are adjusted such that all output signals are synchronized with one another or such that the outputs of the filters differ from each other by the predetermined number of samples.

In the case in which the integrated filter 510 includes one or more LPFs and one or more DLPFs, the duplicated configuration of the LPFs and the DLPFs may be partially combined.

Figure 6A:
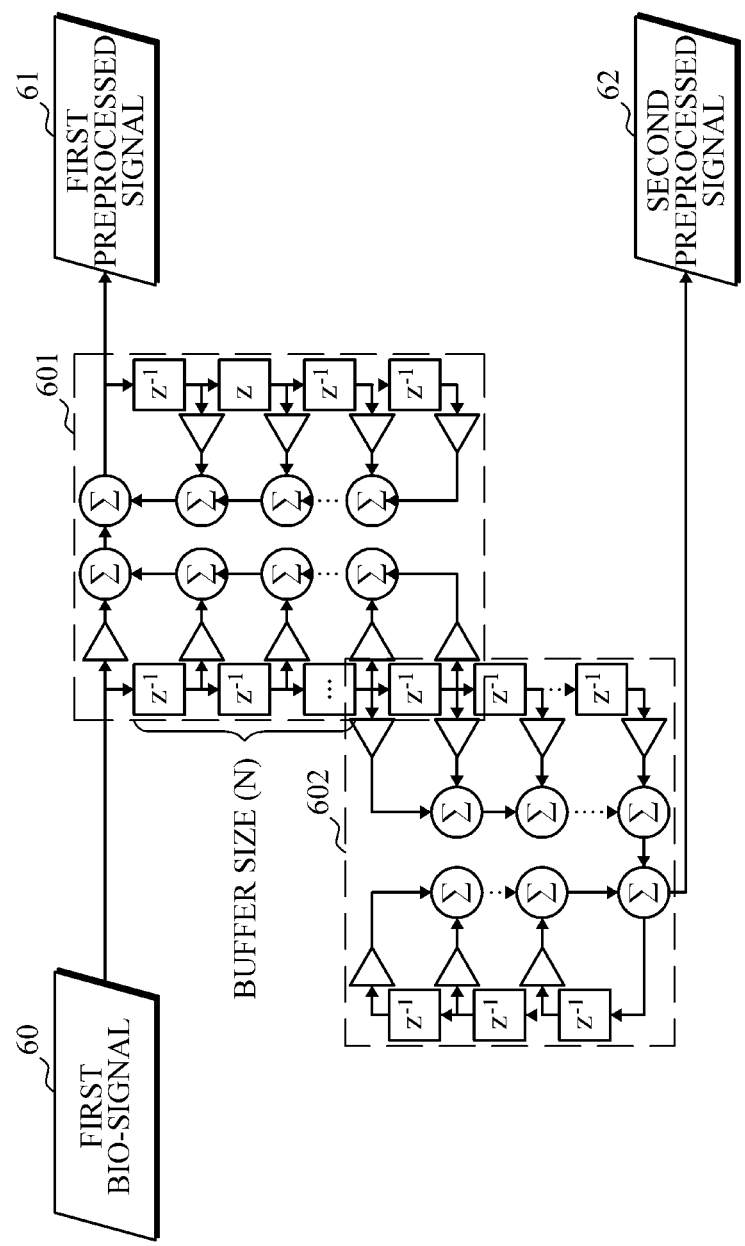
FIG. 6A is a diagram for describing a configuration of an integrated filter according to an exemplary embodiment.

FIG. 6A is a diagram for describing a configuration of an integrated filter according to an exemplary embodiment. Referring to FIG. 6A, an LPF 601 and a DLPF 602 are integrated into the integrated filter 510 of FIG. 5, and one or more circuit components of the integrated filter 510 are operated as part of the LPF 601 and also as part of the DLPF 602. That is, the LPF 610 and the DLPF 602 share one or more identical circuit components. Each of the LPF 601 and the DLPF 602 may be implemented as having an infinite impulse response (IIR) filter structure as shown in FIG. 6A. For example, the LPF 601 of the IIR filter-based integrated filter 510 includes a buffer, and the DLPF 602 partially shares the buffer with the LPF 601, so that the number N of delay buffers for synchronization may be reduced.

The buffer size (N) shown in FIG. 6A corresponds to the delay buffer size. The delay buffer in FIG. 6A is shown as being connected to the LPF 601, i.e., the first LPF. However, the delay buffer is not necessarily connected to the first LPF and can also be connected to the second LPF, and the delay can be adjusted. Thus, referring to FIG. 6A, the buffer size associated with the first LPF 601 is an example and can also be interpreted as the total buffer size of the integrated filter.

When a first bio-signal 60 is input, the integrated filter 510 may output a first preprocessed signal 61 passing through the LPF 601 and a second preprocessed signal 62 passing through the DLPF 602. As such, by sharing the duplicated elements, the buffer size may be reduced. However, the exemplary embodiment is not limited to the above description, and the integrated filter 510 may be implemented with a of a finite impulse response (FIR) filter structure. The more buffers are provided for implementing the LPF and the DLPF, the more effectively the number of delay buffers may be reduced.

Figure 6B:
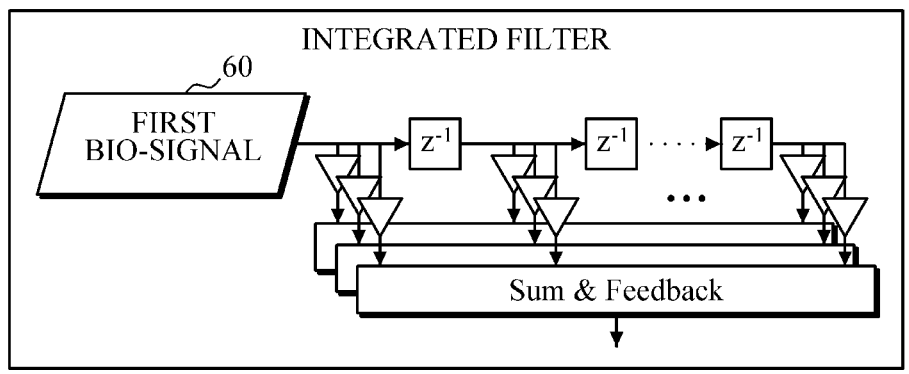
FIG. 6B is a diagram for describing a configuration of an integrated filter according to another exemplary embodiment.

FIG. 6B is a diagram for describing a configuration of an integrated filter according to another exemplary embodiment. Referring to FIGS. 6A and 6B, the integrated filter 510 of FIG. 5 may be implemented with one or more LPFs having an FIR filter structure, and the LPFs may be connected in parallel with each other and output a first to an n-th preprocessed signals. In addition, the integrated filter 510 may output the first to the n-th preprocessed signals whose amount of delays are adjusted by adjusting the size N of the delay buffer connected to the LPFs.

Figure 6C:
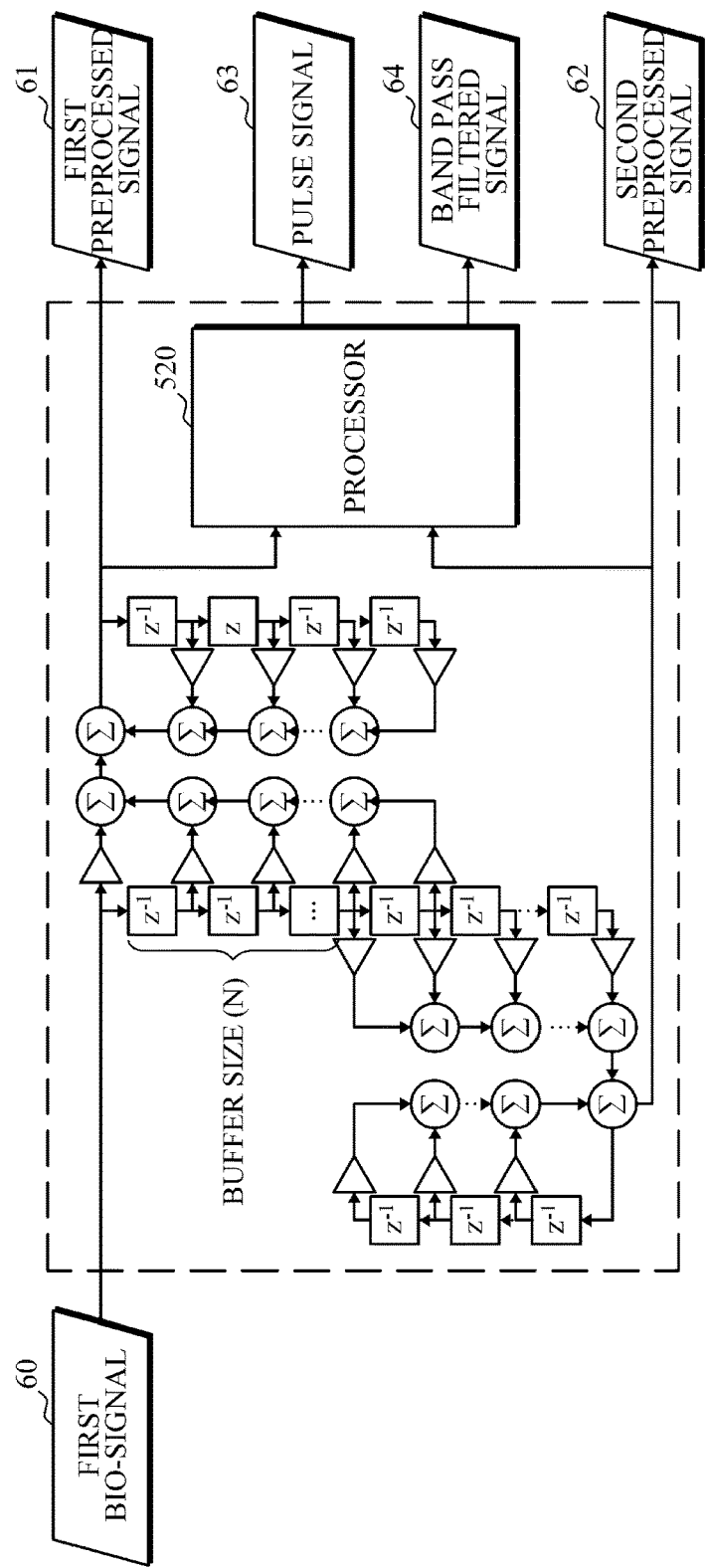
FIG. 6C is a diagram for describing a processor of a bio-signal processing apparatus according to an exemplary embodiment.

FIG. 6C is a diagram for describing a processor of a bio-signal processing apparatus according to an exemplary embodiment.

Referring to FIGS. 5 and 6C, the processor 520 of FIG. 5 may output the second bio-signal 53 for bio-signal detection using a first preprocessed signal 51 and a second preprocessed signal 52 that are preprocessed in the integrated filter 510. Here, the second bio-signal 53 may include a heartbeat signal, a signal in which high frequency and low frequency noises are removed, an input first bio-signal, a pulse signal, and a signal for quality assessment of the input first bio-signal, but is not limited thereto. The second bio-signal 53 may include various preprocessed signals for biometric information detection.

For example, the processor 520 may output a pulse signal 63 by adjusting the amounts of delay of the first preprocessed signal 61 and the second preprocessed signal 62 and comparing the magnitudes of the first preprocessed signal 61 and the second preprocessed signal 62. In one example, in the case in which the integrated filter 510 includes the first LPF and the second LPF and cutoff frequencies of the first LPF and the second LPF are set to be the same, the integrated filter 510 in which a delay buffer may be connected to the input port and/or the output port of the second low pass filter may adjust the amount of delay such that the output of the second low pass filter is delayed by 10 samples relative to the output of the first low pass filter. In this case, the processor 520 may output the pulse signal 63 by extracting only the region in which the first preprocessed signal 61 is greater than the second preprocessed signal 62, using a comparator.

In this case, the processor 520 may extract a contraction/relaxation cycle and a signal for quality assessment of the input first bio-signal 60, using periodicity and irregularity of the extracted pulse signal 63.

For example, in the case in which the input first bio-signal is a cardiac contraction/relaxation cycle signal and includes a little noise, the extracted pulse signal may exhibit a periodicity similar to that of the cardiac contraction/relaxation cycle signal. On the contrary, in the case in which the input first bio-signal includes signals of various frequency ranges, including noise such as motion noise, the pulse signal may be extracted irregularly without periodicity. When the extracted pulse signal has a periodicity and forms a periodic group of a predetermined number of samples, the processor 520 may extract the pulse group as a cardiac contraction/relaxation cycle signal and extract a signal for quality assessment of the input first bio-signal using the irregularity of the extracted pulse signal.

In another example, the processor 520 may output, as the second bio-signal 53, a band pass filtered signal 64 in which high frequency and low frequency noises are removed using the first preprocessed signal 61 and second preprocessed signal 62 that are synchronized with each other. For example, in the case in which the integrated filter 510 includes a first low pass filter and a second low pass filter and the cutoff frequencies of the first low pass filter and the second low pass filter are set to be different from each other, the output of the low pass filter having a lower cutoff frequency may be further delayed and output, and the integrated filter 510 may adjust the size of the delay buffer on the basis of the amount of delay of the further delayed output and delay the other output signal so that the output signals may be synchronized with each other. In this case, the processor 520 may sum the first preprocessed signal 61 and the second preprocessed signal 62 to output the band pass filtered signal 64 in which high frequency and low frequency noises are removed. In this case, the processor 520 may include one or more adders.

As described above with reference to FIGS. 5 and 6C, the bio-signal processing apparatus 500 according to an exemplary embodiment may be implemented with a structure into which the LPF and DLPF are integrated, and may output the first preprocessed signal 61, the second preprocessed signal 62, the pulse signal 63, and the band pass filtered signal 64 from the input first bio-signal 60.

Figure 7:
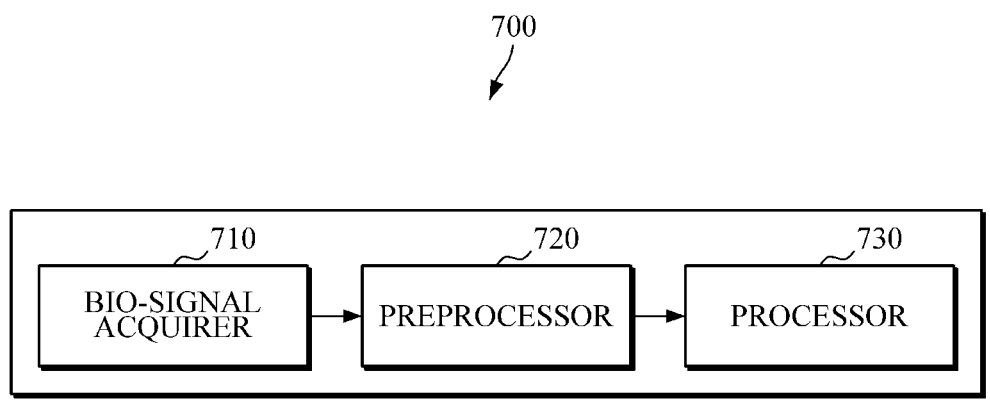
FIG. 7 is a block diagram illustrating a biometric information detection apparatus according to an exemplary embodiment.

FIG. 7 is a block diagram illustrating a biometric information detection apparatus according to an exemplary embodiment. Referring to FIG. 7, a biometric information detection apparatus 700 includes a bio-signal acquirer 710, a preprocessor 720, and a processor 730. The preprocessor 720 and the processor 730 may each be implemented with one or more processors, memories, and one or more modules including them.

The bio-signal acquirer 710 may include a sensor capable of sensing various bio-signals including a bioelectrical signal, a biomechanical signal, a bio-acoustic signal, and a bio-optical signal. For example, the bio-signal acquirer 710 may include a photo sensor that emits light to a subject and detects light scattered or reflected from the subject. In this case, the photo sensor may include a light source configured to emit light in the near infrared ray (NIR) band or the middle infrared ray (MIR) band, but is not limited thereto. In addition, the light source may include a light emitting diode (LED) or a laser diode, and the photo sensor may include a detector, such as a photo transistor (PTr) or a charge-coupled device (CCD), but is not limited thereto.

For example, the bio-signal acquirer 710 may acquire a photoplethysmogram (PPG) signal by emitting light to the user's wrist and detecting light returning from the wrist. In addition, the bio-signal acquirer 710 may acquire a bioelectrical signal, such as electroencephalogram (EEG), electromyography, (EMG), or electrooculogram (EOG), from electrodes attached onto the subject.

The preprocessor 720 may include one or more LPFs, preprocess an input bio-signal and output the preprocessed signal. For example, according to the characteristics and the purpose of use of biometric information (e.g., a heart rate, a cardiac contraction/relaxation cycle, a blood pressure, a degree of arterial aging, a blood sugar level, EEG, EMG, EOG, etc.) to be detected, the preprocessor 720 may appropriately adjust the amounts of delay of a first preprocessed signal and a second preprocessed signal or synchronize output signals with each other. For example, the LPF is characterized in that the lower a cutoff frequency thereof is set, the more an output is delayed relative to an input signal, and accordingly, the preprocessor 720 may include a delay buffer to adjust the amount of delay of an output signal.

For example, the preprocessor 720 may adjust the amount of degree such that the output signals are synchronized with each other. In one example, when the preprocessor 720 includes one or more LPFs, a first preprocessed signal is delayed by 220 samples relative to an input signal and then output from a first LPF and a second preprocessed signal is delayed by 22 samples relative to the input signal and then output from a second LPF, the preprocessor 720 may adjust the amount of delay of the output signal by connecting the delay buffer to an input port and/or an output port of the second LPF such that the second preprocessed signal is further delayed by 198 samples.

In another example, the preprocessor 720 may appropriately adjust the amount of delay of the output signal by connecting the delay buffer to the input port and/or the output port of the LPF. For example, when the preprocessor 720 may include a first LPF and a second LPF that differ in their cutoff frequencies and the first LPF and the second LPF output a first preprocessed signal and a second preprocessed signal, respectively, the preprocessor 720 may adjust the amount of delay of the output signal by connecting the delay buffer to the input port and/or the output port of the first LPF and/or the second LPF buffer so that the amounts of delay of the first preprocessed signal and the second preprocessed signal become 10 samples.

The preprocessor 720 may include one or more LPFs and the LPFs may be implemented independently of each other and process the acquired bio-signal in a parallel manner. For example, in the case in which the preprocessor 720 includes the first LPF and the second LPF, the first LPF and the second LPF may be implemented independently of each other and process the acquired bio-signal in parallel with each other. In addition, the delay buffer to adjust the amount of delay of the preprocessed signal to be output may be independently connected to the input port and/or the output port of the first LPF and/or the second LPF, and adjust the amount of delay of the output signal of each LPF.

In another example, the preprocessor 720 may include one or more LPFs, and the LPFs may be implemented as an integrated filter into which the LPFs are combined and process the acquired bio-signal in an integrated manner. For example, in the case in which the preprocessor 720 includes the first LPF and the second LPF, the first LPF and the second LPF may be coupled to each other in a manner that they share a buffer, and the delay buffer for adjusting the amount of delay of the preprocessed signal to be output may be connected to the input port and/or the output port of the first LPF and/or the second LFP in a manner that the buffer is shared and may adjust the amount of delay of the output signal. In one example, the first LPF and the second LPF may be implemented in a manner that they share a buffer on the basis of an IIR filter structure or an FIR filter structure.

The processor 730 may detect biometric information by processing the output preprocessed signal. For example, the processor 730 may sum up the first preprocessed signal and the second preprocessed signal and detect the biometric information on the basis of a band pass filtered signal in which high frequency and low frequency noises are removed. In one example, when the first preprocessed signal and the second preprocessed signal that are synchronized in the preprocessor 720 have cutoff frequencies of 0.5 Hz and 5 Hz, respectively, the processor 730 may output a band pass filtered signal having a pass band of 0.5 Hz to 5 Hz, using a difference between the first preprocessed signal and the second preprocessed signal. Because a pulse signal has a frequency of about 0.83 Hz to 3.33 Hz, 50 to 200 cycles per minute, an output of the processor 730 having a corresponding frequency may be used to detect a pulse signal.

Figure 8:
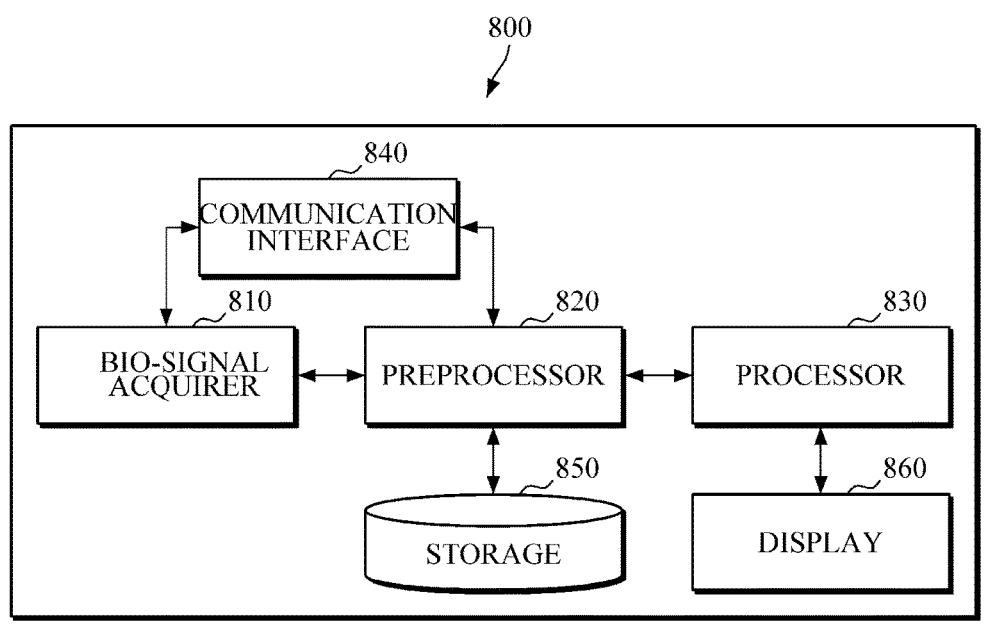
FIG. 8 is a block diagram illustrating a biometric information detection apparatus according to another exemplary embodiment.

FIG. 8 is a block diagram illustrating a biometric information detection apparatus according to another exemplary embodiment. Referring to FIG. 8, a biometric information detection apparatus 800 includes a bio-signal acquirer 810, a preprocessor 820, a processor 830, a communication interface 840, a storage 850, and a display 860. In this case, the bio-signal acquirer 810, the preprocessor 820, and the processor 830 perform the substantially the same functions of those of the bio-signal acquirer 710, the preprocessor 720, and the processor 730, and hence the following description will focus on elements that are not duplicated.

The communication interface 840 may be connected to a bio-signal acquisition apparatus through a wired/wireless network and may obtain, in real-time, bio-signal data from the bio-signal acquisition apparatus, or may receive bio-signal data from an external storage device. For example, the communication interface 840 may access an external device and acquire bio-signal data in response to a control instruction from the processor 830, and may transmit user's biometric information detected by the processor 830 to the external device.

In this case, the external device may be medical equipment that uses a measured bio-signal, a printer for outputting a result, or a display device to display estimated skin condition information. Additionally, the external device may be a digital TV, a desktop computer, a mobile phone, a smart phone, a tablet computer, a notebook computer, a personal digital assistant (PDA), a portable multimedia player, a navigation system, an MP3 player, a digital camera, a wearable device, and an electronic device for processing digital signals, but is not limited thereto.

In addition, the communication interface 840 may include one or more modules for communicating via Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like.

The storage 850 may store the acquired biometric information, preprocessed signals, biometric information detection result, user's personal information, and various types of information. For example, the storage 850 may classify and store the preprocessing result of the acquired bio-signal into different categories according to the amount of delay and may store the operation (e.g., summation, comparison, etc.) of the preprocessed signals. In addition, the storage 850 is not limited to the above example, and may store and manage the biometric information by subdividing the categories for each user and detection target biometric information (e.g., heart rate, cardiac contraction/relaxation cycle, a blood pressure, a degree of arterial aging, a blood sugar level, EEG, EMG, EOG, etc.).

In this case, the storage 850 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, but is not limited thereto.

The display 860 may output various types of information including one or more preprocessed signals output from the preprocessor 820 and the biometric information detection result of the processor 830 to the user. For example, the display 860 may be a touchable display that displays a first preprocessed signal, a second preprocessed signal, and the biometric information detection result in different sections and includes a user interface (UI) through which the amount of delay of the preprocessed signal is adjusted or the operation (e.g., summation, comparison, etc.) of the preprocessed signal is selected.

Figure 9:
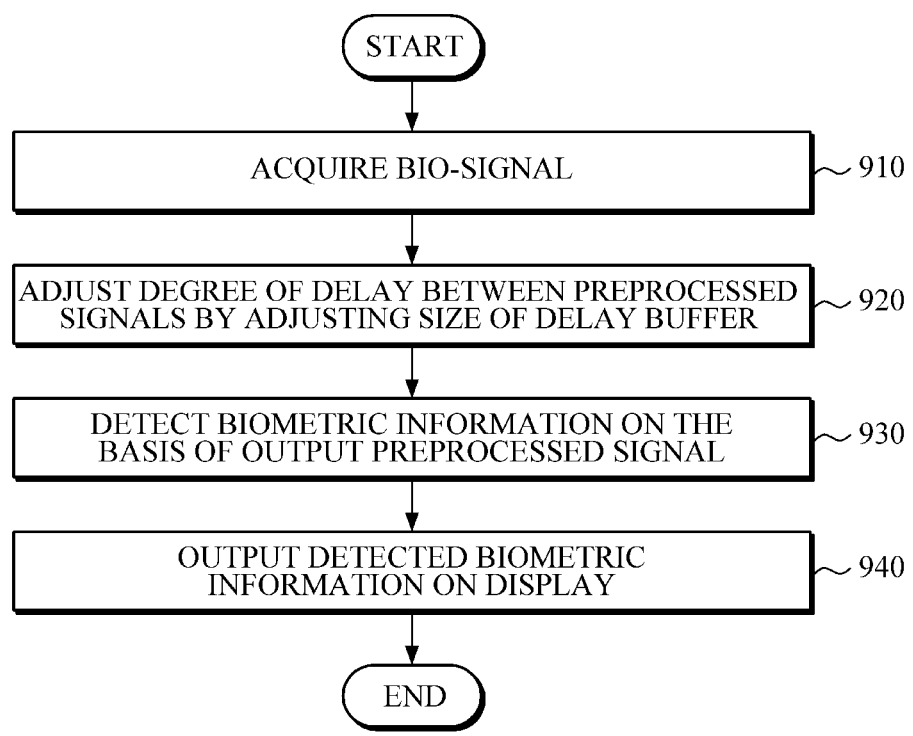
FIG. 9 is a flowchart illustrating a biometric information detection method according to an exemplary embodiment.

FIG. 9 is a flowchart illustrating a biometric information detection method according to an exemplary embodiment. The biometric information detection method of FIG. 9 may be one example of a method performed by the biometric information detection apparatus 800 of FIG. 8 to detect biometric information.

In operation 910, the biometric information detection apparatus 800 acquires a bio-signal from a sensor capable of detecting various bio-signals including a bioelectrical signal, a biomechanical signal, a bio-acoustic signal, and a bio-optical signal. For example, the biometric information detection apparatus 800 may acquire a bio-optical signal by emitting light to a subject and detecting scattered or reflected from the subject.

In operation 920, the biometric information detection apparatus 800 may preprocess the acquired bio-signal according to the characteristics and the purpose of use of biometric information (e.g., a heart rate, a cardiac contraction/relaxation cycle, a blood pressure, a degree of arterial aging, a blood sugar level, EEG, EMG, EOG, etc.) to be detected. Further, the biometric information detection apparatus 800 adjusts a degree of delay between the preprocessed signals by adjusting the size of a delay buffer.

For example, the biometric information detection apparatus 800 may appropriately adjust the amount of delay of the preprocessed signal and synchronize output signals with each other. In one example, in the case in which the biometric information detection apparatus 800 outputs one or more preprocessed signals from one or more LPFs, the biometric information detection apparatus 800 may adjust the amount of delay of the output signal by connecting the delay buffer to an input port and/or an output port of any LPF, and at this time, on the basis of the output of an LPF that delays the output the most, the amount of delay may be adjusted by connecting the delay buffer to an input port and/or an output port of another LPF.

In operation 930, the biometric information detection apparatus 800 detects biometric information on the basis of the output preprocessed signal. For example, when the biometric information detection apparatus 800 detects a pulse signal, using a band pass filtered signal in which high frequency and low frequency noises are removed, the biometric information detection apparatus 800 may output a signal having a predetermined pass band by summing synchronized preprocessed signals. For example, when a first preprocessed signal and a second preprocessed signal are set to have different cutoff frequencies and the first and second preprocessed signals are synchronized with each other and then output through the delay buffer, the biometric information detection apparatus 800 may extract a band pass filtered signal in which high frequency and low frequency noises are removed on the basis of a magnitude difference between the first preprocessed signal and the second preprocessed signal. For example, the biometric information detection apparatus 800 may extract the band pass filtered signal in which high frequency and low frequency noises are removed by summing up the second preprocessed signal, which is synchronized with the first preprocessed signal by adjusting the amount of delay, and the first preprocessed signal that is inverted with respect to a time axis (e.g., x-axis). In this case, the biometric information detection apparatus 800 may detect the pulse signal by setting a pass band to 0.5 to 5 Hz.

In another example, when the biometric information detection apparatus 800 detects a heartbeat signal, using a pulse signal of the preprocessed signal, the biometric information detection apparatus 800 may output the pulse signal by comparing the magnitudes of the first and second preprocessed signals that are adjusted to have a predetermined amount (e.g., 10 samples) of delay therebetween, and extracting only the region in which the first preprocessed signal is greater than the second preprocessed signal. In this case, the biometric information detection apparatus 800 may extract a signal for quality assessment of the heartbeat signal and an input first bio-signal, using the output pulse signal. In one example, in the case in which a first cutoff frequency and a second cutoff frequency are set to be different from each other and one of the first preprocessed signal and the second preprocessed signal is delayed by a predetermined time relative to the other preprocessed signal, the biometric information detection apparatus 800 may compare the magnitudes of the first preprocessed signal and the second preprocessed signal at the same time point with respect to the time axis, determine an irregularity of a region in which one of the first preprocessed signal and the second preprocessed signal is greater than the other, and extract a signal for quality assessment of the input first bio-signal from a second bio-signal on the basis of the determined irregularity.

For example, in the case in which the input first bio-signal is a cardiac contraction/relaxation cycle signal and includes a little noise, the extracted pulse signal may exhibit a periodicity similar to that of the cardiac contraction/relaxation cycle signal. On the contrary, in the case in which the input first bio-signal includes signals of various frequency ranges, including noise such as motion noise, the pulse signal may be extracted irregularly without periodicity. When the extracted pulse signal has a periodicity and forms a periodic group of a predetermined number of samples, the biometric information detection apparatus 800 may extract the pulse group as a cardiac contraction/relaxation cycle signal and extract a signal for quality assessment of the input first bio-signal, using the irregularity of the extracted pulse signal.

In operation 940, the biometric information detection apparatus 800 outputs or displays the detected biometric information on a display. For example, the biometric information detection apparatus 800 may output various types of information including one or more preprocessed signals and the biometric information detection result to the user. In one example, the biometric information detection apparatus 800 may display the detected biometric information on a touchable display that displays the first preprocessed signal, the second preprocessed signal, and the biometric information detection result in different sections and includes a user interface (UI) through which the amount of delay of the preprocessed signal is adjusted or the operation (e.g., summation, comparison, etc.) of the preprocessed signal is selected.

The first LPF and the second LPF that output the first preprocessed signal and the second preprocessed signal, respectively, may be configured as either FIR filters or IIR filters and share one or more buffers to adjust the amounts of delay of outputs of the first LPF and the second LPF. For example, the IIR filter-based LPF includes a buffer, and a DLPF shares partially the buffer with the LPF, so that a structure that effectively reduces the number of delay buffers may be implemented. However, the aspects of the present disclosure are not limited to the above example, and the LPF may be implemented with an FIR filter structure. The more buffers used for implementing the LPF and the DLPF are provided, the more effectively the number of delay buffers used by the LPF may be reduced.

Figure 10:
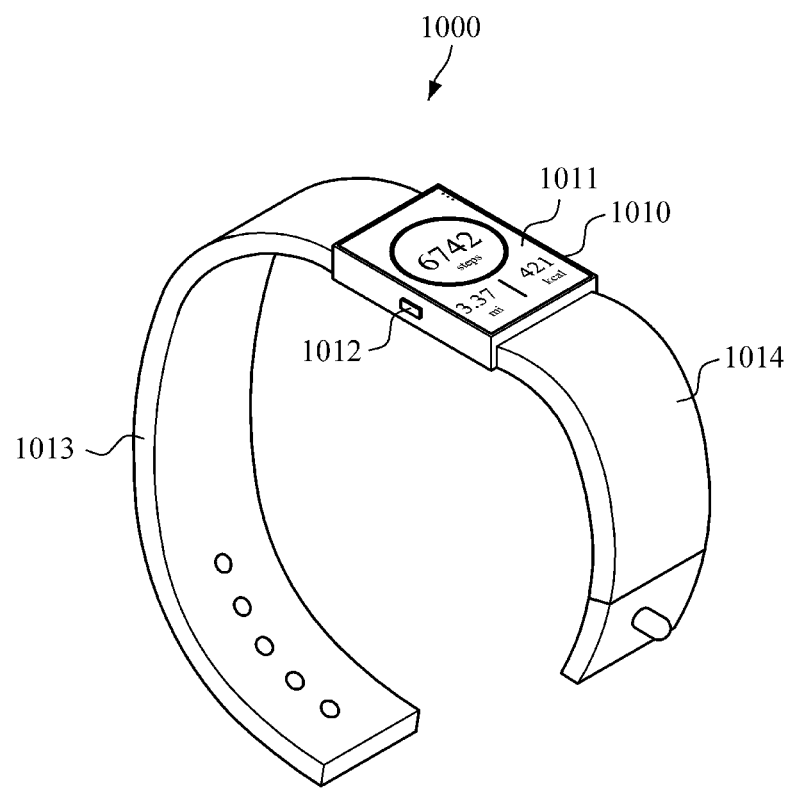
FIG. 10 is a perspective view of a wearable device according to an exemplary embodiment.
Figure 11:
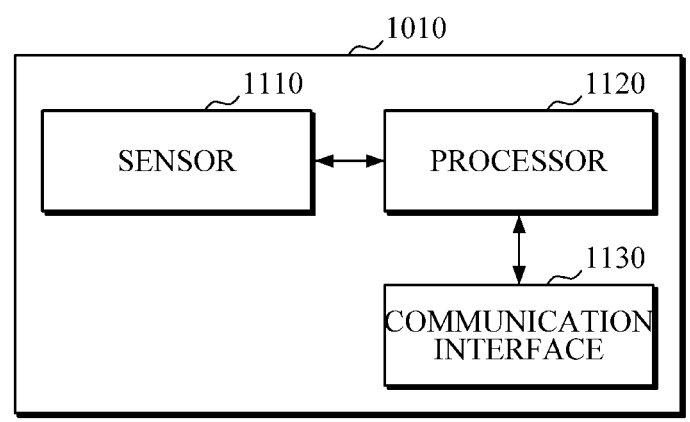
FIG. 11 is a block diagram illustrating components that are mounted in a main body of the wearable device according to an exemplary embodiment.

FIG. 10 is a perspective view of a wearable device according to an exemplary embodiment. FIG. 11 is a block diagram illustrating components that are mounted in a main body of the wearable device according to an exemplary embodiment.

Exemplary embodiments of the biometric information detection apparatus may be mounted in a smart band-type wearable device, as shown in FIGS. 10 and 11. However, this is an example for convenience of description, and thus it may not be construed that the exemplary embodiments are applied to the smart band-type wearable device only.

Referring to FIGS. 10 and 11, the wearable device 1000 includes a main body 1010 and a strap including strap members 1013 and 1014, and the main body 1010 includes a sensor 1110, a processor 1120, and a communication interface 1130.

The strap may be formed to be flexible, and may be bent to wrap around or be separated from the user's wrist. In this case, a battery for supplying power to the wearable device may be installed inside the main body 1010 or the strap members 1013 and 1014.

In addition, the sensor 1110 for detecting a user's bio-signal may be included in the main body 1010 of the wearable device 1000. For example, the sensor 1110 may include a spectrometer that emits light to the user's skin and measures a spectrum of light through spectroscopy of the light scattered or reflected from the skin. In addition, the strap members 1013 and 1014 may be formed of a variable resistance material to measure a resistance change according to the user's pulse. However, this is an exemplary embodiment, and the aspects of the present disclosure are not limited to the above, such that the sensor 1110 may include various types of sensors capable of measuring a bioelectrical signal, biomechanical signal, a bio-acoustic signal, and a bio-optical signal.

The processor 1120 may acquire a bio-signal used for biometric information by controlling the sensor of the sensor 1110 and filter the acquired bio-signal by passing the bio-signal through an LPF. In this case, as the cutoff frequency of the LPF is lowered according to the characteristic of the LPF, the output signal of the LPF is more delayed relative to an input signal and then output. The processor 1120 may adjust the amount of delay of the output by appropriately adjusting the size of a delay buffer at an input port and/or an output port of the LPF.

For example, when the processor 1120 includes one or more LPFs and outputs one or more signals, on the basis of a signal of an LPF that is delayed the most and output due to the lowest cutoff frequency, the processor 1120 may adjust the amount of delay of the output signal or synchronize the output signals by connecting the delay buffer to an input port and/or an output port of another LPF.

The processor 1120 may detect biometric information, using the bio-signal preprocessed by adjusting the amount of delay. For example, because a pulse signal has a frequency of about 0.83 Hz to 3.33 Hz, 50 to 200 cycles per minute, an output of the processor having a corresponding frequency may be used to detect a pulse signal. The processor 1120 may filter the input bio-signal using LPFs whose cutoff frequencies are set 0.5 Hz and 5 Hz, respectively, delay the output of the LPF having a cutoff frequency of 5 Hz to synchronize the two output signals of the LPFs, invert the signal filtered by the LPF having a lower cutoff frequency with respect to a time axis, and output a signal in which high frequency and low frequency noises are removed by summing up the two output signals, thereby detecting a pulse signal.

The processor 1120 may control the sensor 1110 on the basis of a result of quality assessment of the bio-signal detected by the sensor 1110. For example, when the detected bio-signal includes a large amount of noise and hence is assessed to be of poor quality, the processor 1120 may emit more amount of light to the skin by controlling the sensor 1110 to adjust the amount of light irradiated to the skin and re-detect a bio-signal. On the contrary, when the quality of the detected bio-signal is assessed to be good, the processor 1120 may reduce the amount of light emitted to the skin by controlling the sensor 1110 to save the power consumption. As such, the processor 1120 may control various sensors (e.g., a spectrometer, a detector, etc.) included in the sensor 1110 on the basis of the result of assessing a quality of the input first bio-signal and flexibly acquire the bio-signal.

The processor 1120 may include one or more LPFs and filter the input bio-signal. In this case, the LPFs may be configured as either FIR filters or IIR filters. For example, the IIR filter-based LPF includes a buffer and a DLPF shares partially the buffer with the LPF, so that a structure that effectively reduces the number of delay buffers may be implemented.

The communication interface 1130 may transmit information to the user's portable terminal, which has a relatively high computing performance, according to the control of the processor 1120, thereby providing the information to the user. In addition, the communication interface 1130 may be connected to a biometric information database (DB) in a wired/wireless communication manner to receive biometric information and transmit detected biometric information, according to a biometric information transmission/reception instruction of the processor 1120. For example, the communication interface 1130 may be connected to an external bio-signal measurement apparatus capable of measuring a user's bio-signal and receive a bio-signal, other than the bio-signal sensed by the sensor 1110, and may transmit the detected biometric information to the external biometric information DB or to a user's portable terminal in response to a control instruction of the processor 1120.

The wearable device 1000 further includes an operator 1012 and a display 1011 that are mounted in the main body 1010.

The operator 1012 may receive a control command of the user, transmit the control command to the processor 1120, and include a power button for inputting a command to turn on/off the power of the wearable device 1000.

The display 1011 may display various types of information including the biometric information detection result to the user. For example, the display 1011 may be implemented as a touchable display that displays a first preprocessed signal, a second preprocessed signal, and the biometric information detection result in different sections and includes a user interface (UI) through which the amount of delay of the preprocessed signal is adjusted or the operation (e.g., summation, comparison, etc.) of the preprocessed signal is selected.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-signal processing apparatus comprising:
  a first low pass filter (LPF) configured to have a first cutoff frequency, and output a first preprocessed signal having low frequency components of an input bio-signal that are less than the first cutoff frequency;
  a second LPF configured to have a second cutoff frequency, and output a second preprocessed signal in which high frequency components greater than or equal to the second cutoff frequency are removed from the input bio-signal;
  a delay buffer configured to adjust amounts of delay of the output second preprocessed signal and the output first preprocessed signal, wherein a size of the delay buffer is adjusted based on a difference between the first cutoff frequency and the second cutoff frequency to synchronize the output first preprocessed signal and the output second preprocessed signal; and
  a processor configured to output an output bio-signal for biometric information detection, based on the output first preprocessed signal and the output second preprocessed signal that are synchronized.

2. The bio-signal processing apparatus of claim 1, wherein the input bio-signal is input, in parallel, to the first LPF and the second LPF, and
  the first LPF and the second LPF are further configured to filter the input bio-signal in a parallel manner.

3. The bio-signal processing apparatus of claim 1, wherein the delay buffer is connected to either one or both of an input port and an output port of the second LPF.

4. The bio-signal processing apparatus of claim 1, wherein the processor is further configured to, in response to the first cutoff frequency and the second cutoff frequency being set to be equal, and one of the output first preprocessed signal and the output second preprocessed signal being delayed by a predetermined time relative to another one of the output first preprocessed signal and the output second preprocessed signal, through the delay buffer, compare a magnitude of the output first preprocessed signal and a magnitude of the output second preprocessed signal to generate the output bio-signal.

5. The bio-signal processing apparatus of claim 4, wherein the processor is further configured to:
  determine, in the generated output bio-signal, a periodicity of a time interval in which the one of the output first preprocessed signal and the output second preprocessed signal is greater than the other of the output first preprocessed signal and the output second preprocessed signal; and
  extract a cardiac contraction/relaxation cycle from the generated output bio-signal, based on the determined periodicity.

6. The bio-signal processing apparatus of claim 1, wherein the processor is further configured to, in response to the first cutoff frequency and the second cutoff frequency being set to be different, and the output first preprocessed signal and the output second preprocessed signal being synchronized through the delay buffer:
  compare a magnitude of the output first preprocessed signal and a magnitude of the output second preprocessed signal to generate the output bio-signal; and
  detect an error of the generated output bio-signal, based on an amount of change in time between pulse signals of the generated output bio-signal.

7. The bio-signal processing apparatus of claim 1, wherein the processor is further configured to, in response to the first cutoff frequency and the second cutoff frequency being set to be different, and the output first preprocessed signal and the output second preprocessed signal being synchronized through the delay buffer, generate the output bio-signal, based on a difference in magnitude between the first preprocessed signal and the second preprocessed signal that are synchronized.

8. The bio-signal processing apparatus of claim 1, wherein the processor is further configured to, in response to the first cutoff frequency and the second cutoff frequency being set to be different, and one of the output first preprocessed signal and the output second preprocessed signal being delayed by a predetermined time relative to another one of the output first preprocessed signal and the output second preprocessed signal, through the delay buffer:
  compare a magnitude of the output first preprocessed signal and a magnitude of the output second preprocessed signal at same time points to generate the output bio-signal;
  determine, in the generated output bio-signal, an irregularity of a time interval in which the one of the first preprocessed signal and the second preprocessed signal is greater than the other of the first preprocessed signal and the second preprocessed signal; and
  extract a signal for quality assessment of the input bio-signal from the generated output bio-signal, based on the determined irregularity.

9. The bio-signal processing apparatus of claim 1, wherein the first LPF and the second LPF comprise finite impulse response (FIR) filters or infinite impulse response (IIR) filters.

10. The bio-signal processing apparatus of claim 1, wherein the output bio-signal comprises any one or any combination of a heartbeat signal, a cardiac contraction/relaxation cycle signal, a signal in which high frequency and low frequency noises are removed, the input bio-signal, and a signal for quality assessment of the input bio-signal.

11. The bio-signal processing apparatus of claim 1, further comprising an integrated filter comprising the first LPF and the second LPF.

12. A biometric information detection apparatus comprising:
  a bio-signal acquirer configured to acquire a bio-signal from a subject;
  a preprocessor comprising:
    a first low pass filter (LPF) configured to have a first cutoff frequency, and output a first preprocessed signal having low frequency components of the acquired bio-signal that are less than the first cutoff frequency; and
    a second LPF configured to have a second cutoff frequency, and output a second preprocessed signal in which high frequency components greater than or equal to the second cutoff frequency are removed from the acquired bio-signal; and
  a processor configured to:
    detect biometric information, based on the output first preprocessed signal and the output second preprocessed signal; and control the bio-signal acquirer to, based on a result of assessing a quality of the acquired bio-signal, re-acquire a bio-signal from the subject.

13. The biometric information detection apparatus of claim 12, wherein the biometric information comprises any one or any combination of a heartbeat signal, a cardiac contraction/relaxation cycle signal, a blood pressure, a degree of arterial aging, a blood sugar level, electroencephalogram (EEG), electromyography, (EMG), and electrooculogram (EOG).

14. The biometric information detection apparatus of claim 12, wherein the preprocessor further comprises a delay buffer connected to an input port or an output port of the second LPF, and configured to adjust amounts of delay of the output first preprocessed signal and the output second preprocessed signal.

15. The biometric information detection apparatus of claim 12, wherein the first LPF and the second LPF are implemented independently, and further configured to filter the acquired bio-signal in a parallel manner.

16. The biometric information detection apparatus of claim 12, wherein the first LPF and the second LPF are implemented as an integrated filter into which the first and second LPFs are combined, and further configured to integrally filter the acquired bio-signal.

17. The biometric information detection apparatus of claim 12, wherein the bio-signal acquirer is further configured to acquire the bio-signal by emitting light to the subject and detecting light scattered or reflected from the subject.

18. The biometric information detection apparatus of claim 12, further comprising:
a communication interface configured to receive bio-signal data that is stored in an external storage device; and
a display configured to display the acquired bio-signal, the output first preprocessed signal, the output second preprocessed signal, and the detected biometric information.

19. A method of detecting biometric information comprising:
acquiring a bio-signal from a subject;
outputting, by a first low pass filter (LPF), a first preprocessed signal having low frequency components of the acquired bio-signal that are less than a first cutoff frequency;
outputting, by a second LPF, a second preprocessed signal in which high frequency components greater than or equal to a second cutoff frequency are removed from the acquired bio-signal;
adjusting, by a delay buffer, amounts of delay of the output second preprocessed signal and the output first preprocessed signal, wherein a size of the delay buffer is adjusted based on a difference between the first cutoff frequency and the second cutoff frequency to synchronize the output first preprocessed signal and the output second preprocessed signal; and
detecting biometric information, based on the output first preprocessed signal and the output second preprocessed signal that are synchronized.

20. The method of claim 19, further comprising displaying the acquired bio-signal, the output first preprocessed signal, the output second preprocessed signal, and the detected biometric information.

21. A wearable device comprising:
a sensor configured to detect a bio-signal of a user;
a processor configured to:
control the sensor to detect the bio-signal;
filter the detected bio-signal through an LPF;
adjust an amount of delay of the filtered bio-signal; and
detect biometric information, based on the filtered bio-signal of which the amount of delay is adjusted;
control the sensor to, based on a result of assessing a quality of the detected bio-signal, re-detect a bio-signal of the user; and
a main body in which the sensor and the processor are disposed.

22. The wearable device of claim 21, further comprising a communication interface disposed in the main body, and configured to receive biometric information from a biometric information database (DB),
wherein the processor is further configured to control the communication interface to transmit the detected biometric information to the biometric information DB.

23. The wearable device of claim 21, further comprising a display disposed in the main body, and configured to display the detected biometric information.

24. The wearable device of claim 21, wherein the processor comprises the LPF and another LPF that comprise finite impulse response (FIR) filters or infinite impulse response (IIR) filters, and a delay buffer configured to adjust amounts of delay of outputs of the LPF and the other LPF, and
the processor is further configured to filter the detected bio-signal through the other LPF.

25. A bio-signal processing apparatus comprising:
a first low pass filter (LPF) configured to filter an input bio-signal to generate a first preprocessed signal having low frequency components of the input bio-signal that are less than a first cutoff frequency;
a second LPF configured to filter the input bio-signal to generate a second preprocessed signal in which high frequency components greater than or equal to a second cutoff frequency are removed from the input bio-signal;
a delay buffer configured to delay one of the generated first preprocessed signal and the generated second preprocessed signal; and
a processor configured to:
generate an output bio-signal for biometric information detection, based on the delayed one of the output first preprocessed signal and the output second preprocessed signal and another one of the output first preprocessed signal and the output second preprocessed signal; and
based on a result of assessing a quality of the input bio-signal, control to re-detect an input bio-signal.

26. The bio-signal processing apparatus claim 25, wherein the first cutoff frequency is different than the second cutoff frequency,
the delay buffer is further configured to delay the generated second preprocessed signal to synchronize the generated second preprocessed signal with the generated first preprocessed signal, and
the processor is further configured to invert the generated first preprocessed signal, and add the inverted first preprocessed signal to the synchronized second preprocessed signal to generate a band pass filtered signal as the output bio-signal.

27. The bio-signal processing apparatus claim 25, wherein the first cutoff frequency is different than the second cutoff frequency,
the delay buffer is further configured to delay the generated second preprocessed signal to synchronize the generated second preprocessed signal with the generated first preprocessed signal, and
the processor is further configured to compare the generated first preprocessed signal to the synchronized second preprocessed signal to generate a pulse signal as the output bio-signal.

28. The bio-signal processing apparatus claim 25, wherein the first cutoff frequency is equal to the second cutoff frequency,
- the delay buffer is further configured to delay the generated second preprocessed signal by a predetermined amount of time, and
- the processor is further configured to compare the generated first preprocessed signal to the delayed second preprocessed signal to generate a pulse signal as the output bio-signal.

29. The bio-signal processing apparatus claim 25, wherein the first cutoff frequency is different than the second cutoff frequency,
- the delay buffer is further configured to delay the generated second preprocessed signal by a predetermined amount of time, and
- the processor is further configured to compare the generated first preprocessed signal to the delayed second preprocessed signal to generate a pulse signal as the output bio-signal.

\* \* \* \* \*